(12) United States Patent
Kadish et al.

(10) Patent No.: US 11,419,809 B2
(45) Date of Patent: Aug. 23, 2022

(54) HAIR TREATMENT COMPOSITIONS AND METHODS FOR TREATING HAIR

(71) Applicant: L'OREAL, Paris (FR)

(72) Inventors: Danielle Kadish, Clark, NJ (US); Barbara Joi Mitchell, Teaneck, NJ (US); Kwana Kinetra Patterson, Plainfield, NJ (US); Anand Mahadeshwar, Scotch Plains, NJ (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 16/455,139

(22) Filed: Jun. 27, 2019

(65) Prior Publication Data

US 2020/0405618 A1 Dec. 31, 2020

(51) Int. Cl.

| | | |
|---|---|---|
| A61Q 5/00 | (2006.01) | |
| A61Q 5/06 | (2006.01) | |
| A61K 8/891 | (2006.01) | |
| A61K 8/41 | (2006.01) | |
| A61K 8/84 | (2006.01) | |
| A61K 8/892 | (2006.01) | |
| A61K 8/898 | (2006.01) | |
| A61K 8/34 | (2006.01) | |
| A61K 8/362 | (2006.01) | |

(52) U.S. Cl.
CPC .............. *A61K 8/891* (2013.01); *A61K 8/345* (2013.01); *A61K 8/347* (2013.01); *A61K 8/362* (2013.01); *A61K 8/41* (2013.01); *A61K 8/84* (2013.01); *A61K 8/892* (2013.01); *A61K 8/898* (2013.01)

(58) Field of Classification Search
None
See application file for complete search history.

(56) References Cited

U.S. PATENT DOCUMENTS

| | | |
|---|---|---|
| 2,261,002 A | 10/1941 | Ritter |
| 2,271,378 A | 1/1942 | Searle |
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,674,580 A | 4/1954 | Henkin |
| 2,850,351 A | 9/1958 | Moore et al. |
| 2,961,347 A | 11/1960 | Floyd |
| 3,142,623 A | 7/1964 | Zviak et al. |
| 3,193,464 A | 7/1965 | Edman et al. |
| 3,206,462 A | 9/1965 | McCarty |
| 3,227,615 A | 1/1966 | Korden |
| 3,288,770 A | 11/1966 | Butler |
| 3,412,019 A | 11/1968 | Hoover et al. |
| 3,472,243 A | 10/1969 | Wall et al. |
| 3,472,840 A | 10/1969 | Stone et al. |
| 3,589,978 A | 6/1971 | Kamal et al. |
| 3,632,559 A | 1/1972 | Matter et al. |
| 3,766,267 A | 10/1973 | Zak et al. |
| 3,840,656 A | 10/1974 | Kalopissis et al. |
| 3,874,870 A | 4/1975 | Green et al. |
| 3,917,817 A | 11/1975 | Vanlerberghe et al. |
| 3,929,990 A | 12/1975 | Green et al. |
| 3,966,904 A | 6/1976 | Green et al. |
| 4,001,432 A | 1/1977 | Green et al. |
| 4,003,699 A | 1/1977 | Rose et al. |
| 4,005,193 A | 1/1977 | Green et al. |
| 4,012,398 A | 3/1977 | Conner et al. |
| 4,013,787 A | 3/1977 | Vanlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,166,894 A | 9/1979 | Schaper |
| 4,172,887 A | 10/1979 | Vanlerberghe et al. |
| RE30,199 E | 1/1980 | Rose et al. |

(Continued)

FOREIGN PATENT DOCUMENTS

| | | |
|---|---|---|
| CN | 1383377 A | 12/2002 |
| CN | 1423548 A | 6/2003 |

(Continued)

OTHER PUBLICATIONS

Translation of Chinese Office Action for counterpart Application No. 201680079800.4, dated Aug. 24, 2020.
Search Report for Chinese Application No. 201680079800.4, dated Aug. 24, 2020.
Translation of Chinese Office Action for counterpart Application No. 201680079773.0, dated Aug. 21, 2020.
Search report for counterpart Chinese Application No. 201680079773.0, dated Aug. 21, 2020.
Translation of Japanese Office Action for counterpart Application No. 2018-546409, dated Sep. 7, 2020.
Translation of Chinese Office Action for counterpart Application No. 201680079774.5, dated Sep. 1, 2020.
Fridman, R.A., "Technology of Cosmetics," publ. of "Food Industry," 1964, pp. 3-6, 297-308, 411-428 and 441-466 (translation).
Zefirova, N.S., "Big Russian Encyclopedia," Chemical Encyclopedia, 1995, vol. 4, pp. 183-185 (translation).

(Continued)

*Primary Examiner* — Jyothsna A Venkat
(74) *Attorney, Agent, or Firm* — The Marbury Law Group, PLLC

(57) ABSTRACT

The instant disclosure relates to hair treatment compositions that include a unique combination of components that function to impart desirable cosmetic properties to the hair. The hair treatment compositions typically include a first phase containing a non-polymeric mono, di, or tricarboxylic acid, and/or a salt thereof, an amine, a cationic polymer, an alkoxysilane, polyols, and water; and a second phase containing a film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane, and at least one silicone oil.

27 Claims, 2 Drawing Sheets

(56) References Cited

U.S. PATENT DOCUMENTS

| | | |
|---|---|---|
| 4,189,468 A | 2/1980 | Vanlerberghe et al. |
| 4,197,865 A | 4/1980 | Jacquet et al. |
| 4,217,914 A | 8/1980 | Jacquet et al. |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,412,943 A | 11/1983 | Hirota et al. |
| 4,422,853 A | 12/1983 | Jacquet et al. |
| 4,425,132 A | 1/1984 | Grollier et al. |
| 4,532,950 A | 8/1985 | Lang et al. |
| 4,579,732 A | 4/1986 | Grollier et al. |
| 4,591,610 A | 5/1986 | Grollier |
| 4,608,250 A | 8/1986 | Jacquet et al. |
| 4,734,277 A | 3/1988 | Login |
| 4,761,273 A | 8/1988 | Grollier et al. |
| 4,770,873 A | 9/1988 | Wolfram et al. |
| 4,772,462 A | 9/1988 | Boothe et al. |
| 4,777,040 A | 10/1988 | Grollier et al. |
| 4,793,992 A | 12/1988 | Mathews et al. |
| 4,793,993 A | 12/1988 | Siuta-Mangano et al. |
| 4,812,307 A | 3/1989 | Siuta-Mangano |
| 4,834,971 A | 5/1989 | Klenk et al. |
| 4,855,130 A | 8/1989 | Konrad et al. |
| 4,906,460 A | 3/1990 | Kim et al. |
| 4,948,579 A | 8/1990 | Jacquet et al. |
| 4,970,066 A | 11/1990 | Grollier et al. |
| 5,061,289 A | 10/1991 | Clausen et al. |
| 5,085,860 A | 2/1992 | Junino et al. |
| 5,091,171 A | 2/1992 | Yu et al. |
| 5,143,518 A | 9/1992 | Madrange et al. |
| 5,196,189 A | 3/1993 | Jacquet et al. |
| 5,221,286 A | 6/1993 | Singleton et al. |
| 5,293,885 A | 3/1994 | Darkwa et al. |
| 5,350,572 A | 9/1994 | Savaides et al. |
| 5,356,438 A | 10/1994 | Kim et al. |
| 5,380,340 A | 1/1995 | Neunhoeffer et al. |
| 5,534,267 A | 7/1996 | Neunhoeffer et al. |
| 5,565,216 A | 10/1996 | Cowsar et al. |
| 5,593,662 A | 1/1997 | Deckner et al. |
| 5,616,150 A | 4/1997 | Moeller et al. |
| 5,628,991 A | 5/1997 | Samain et al. |
| 5,635,168 A | 6/1997 | Burns et al. |
| 5,651,960 A | 7/1997 | Chan et al. |
| 5,656,265 A | 8/1997 | Bailey et al. |
| 5,663,366 A | 9/1997 | Neunhoeffer et al. |
| 5,688,291 A | 11/1997 | Said et al. |
| 5,708,151 A | 1/1998 | Möckli |
| 5,750,099 A | 5/1998 | Yoshihara et al. |
| 5,766,576 A | 6/1998 | Lowe et al. |
| 5,785,962 A | 7/1998 | Hinz et al. |
| 5,811,085 A | 9/1998 | Halloran |
| 5,833,966 A | 11/1998 | Samain |
| 5,853,707 A | 12/1998 | Wells et al. |
| 5,869,068 A | 2/1999 | De Lacharriere et al. |
| 5,951,969 A | 9/1999 | Golinski et al. |
| 5,972,322 A | 10/1999 | Rath et al. |
| 5,985,803 A | 11/1999 | Rizvi et al. |
| 6,013,250 A | 1/2000 | Cannell et al. |
| 6,015,574 A | 1/2000 | Cannell et al. |
| 6,036,966 A | 3/2000 | Youssefyeh |
| 6,090,762 A | 7/2000 | Clapperton et al. |
| 6,099,592 A | 8/2000 | Vidal et al. |
| 6,173,717 B1 | 1/2001 | Schonert et al. |
| 6,231,843 B1 | 5/2001 | Hoelzel et al. |
| 6,241,971 B1 | 6/2001 | Fox et al. |
| 6,284,003 B1 | 9/2001 | Rose et al. |
| 6,309,426 B1 | 10/2001 | Dias et al. |
| 6,338,741 B1 | 1/2002 | Vidal et al. |
| 6,348,189 B1 | 2/2002 | Tanabe et al. |
| 6,348,200 B1 | 2/2002 | Nakajima et al. |
| 6,358,502 B1 | 3/2002 | Tanabe et al. |
| 6,398,821 B1 | 6/2002 | Dias et al. |
| 6,458,906 B1 | 10/2002 | Torgerson et al. |
| 6,488,945 B2 | 12/2002 | Sato |
| 6,515,050 B1 | 2/2003 | Mitsuzuka et al. |
| 6,537,532 B1 | 3/2003 | Torgerson et al. |
| 6,562,327 B1 | 5/2003 | Nguyen et al. |
| 6,569,412 B2 | 5/2003 | Yamaguchi et al. |
| 6,645,258 B2 | 11/2003 | Vidal et al. |
| 6,645,478 B2 | 11/2003 | Rollat et al. |
| 6,669,933 B2 | 12/2003 | Duffer et al. |
| 6,706,258 B1 | 3/2004 | Gallagher et al. |
| 6,730,789 B1 | 5/2004 | Birault et al. |
| 6,767,875 B1 | 7/2004 | Snyder et al. |
| 6,979,439 B1 | 12/2005 | Sakai et al. |
| 6,984,250 B1 | 1/2006 | Legrand et al. |
| 7,041,142 B2 | 5/2006 | Chan et al. |
| 7,044,986 B2 | 5/2006 | Ogawa et al. |
| 7,135,167 B2 | 11/2006 | Legrand et al. |
| 7,147,843 B2 | 12/2006 | Koshida et al. |
| 7,151,079 B2 | 12/2006 | Fack et al. |
| 7,204,861 B2 | 4/2007 | Marsh et al. |
| 7,390,479 B2 | 6/2008 | Sockel et al. |
| 7,427,656 B2 | 9/2008 | Decarolis et al. |
| 7,495,037 B2 | 2/2009 | Moszner et al. |
| 7,598,213 B2 | 10/2009 | Geary et al. |
| 7,612,141 B2 | 11/2009 | Sakai et al. |
| 7,815,901 B2 | 10/2010 | Mathonneau et al. |
| 7,905,926 B2 | 3/2011 | DeGeorge et al. |
| 7,915,208 B2 | 3/2011 | Roso et al. |
| 7,931,698 B2 | 4/2011 | Simonet et al. |
| 7,972,388 B2 | 7/2011 | Hamilton et al. |
| 7,981,405 B2 | 7/2011 | Ueyama et al. |
| 8,163,861 B2 | 4/2012 | Puerta et al. |
| 8,241,370 B2 | 8/2012 | Legrand et al. |
| 8,288,329 B2 | 10/2012 | Hata et al. |
| 8,298,519 B2 | 10/2012 | Adams et al. |
| 8,357,356 B2 | 1/2013 | Zaeska et al. |
| 8,388,701 B2 | 3/2013 | Uellner et al. |
| 8,513,200 B2 | 8/2013 | Dixon et al. |
| 8,613,913 B2 | 12/2013 | Chang et al. |
| 8,632,758 B2 | 1/2014 | Terada |
| 8,642,021 B2 | 2/2014 | Brautigam et al. |
| 8,642,659 B2 | 2/2014 | Springer et al. |
| 8,921,292 B2 | 12/2014 | Fujita et al. |
| 9,006,162 B1 | 4/2015 | Rizk |
| 9,044,409 B2 | 6/2015 | Carola et al. |
| 9,095,518 B2 | 8/2015 | Pressly et al. |
| 9,114,088 B2 | 8/2015 | Konno et al. |
| 9,144,537 B1 | 9/2015 | Pressly et al. |
| 9,175,114 B2 | 11/2015 | Puerta et al. |
| 9,180,086 B2 | 11/2015 | Cabourg et al. |
| 9,283,156 B2 | 3/2016 | Savaides et al. |
| 9,326,926 B2 | 5/2016 | Pressly et al. |
| 9,402,796 B2 | 8/2016 | Briggs et al. |
| 9,498,419 B2 | 11/2016 | Pressly et al. |
| 9,597,273 B2 | 3/2017 | Pressly et al. |
| 9,610,241 B2 | 4/2017 | Cabourg et al. |
| 9,849,071 B2 | 12/2017 | Fack et al. |
| 9,918,923 B1 | 3/2018 | Naiberk et al. |
| 9,993,406 B2 | 6/2018 | Manneck et al. |
| 10,004,673 B1 | 6/2018 | Elsen-Wahrer et al. |
| 10,085,931 B2 | 10/2018 | Baghdadli et al. |
| 10,219,994 B2 | 3/2019 | Lechner et al. |
| 10,231,915 B2 | 3/2019 | Dreher et al. |
| 10,561,599 B2 | 2/2020 | Patterson et al. |
| 10,576,307 B2* | 3/2020 | Patterson ............... A61K 8/817 |
| 2001/0029637 A1 | 10/2001 | Nakashimada et al. |
| 2001/0042276 A1 | 11/2001 | Kawasoe et al. |
| 2001/0052354 A1 | 12/2001 | Nishibe et al. |
| 2002/0029429 A1 | 3/2002 | Dias et al. |
| 2002/0032933 A1 | 3/2002 | Dias et al. |
| 2002/0050013 A1 | 5/2002 | Vidal et al. |
| 2002/0053110 A1 | 5/2002 | Dias et al. |
| 2002/0155081 A1 | 10/2002 | Coope |
| 2002/0189034 A1 | 12/2002 | Kitabata et al. |
| 2003/0012761 A1 | 1/2003 | Koshida et al. |
| 2003/0019051 A9 | 1/2003 | Vidal et al. |
| 2003/0049222 A1 | 3/2003 | Akhter et al. |
| 2003/0072962 A1 | 4/2003 | Matsuzaki et al. |
| 2003/0083380 A1 | 5/2003 | Yu et al. |
| 2003/0152543 A1 | 8/2003 | Legrand et al. |

(56) References Cited

U.S. PATENT DOCUMENTS

| | | |
|---|---|---|
| 2003/0215415 A1 | 11/2003 | Mitsumatsu et al. |
| 2004/0034944 A1 | 2/2004 | Legrand et al. |
| 2004/0034946 A1 | 2/2004 | Legrand et al. |
| 2004/0067212 A1 | 4/2004 | Tokuyama et al. |
| 2004/0086475 A1 | 5/2004 | Boswell et al. |
| 2004/0088800 A1 | 5/2004 | Cotteret |
| 2004/0156877 A1 | 8/2004 | Tokuyama et al. |
| 2004/0181883 A1 | 9/2004 | Legrand et al. |
| 2004/0202689 A1 | 10/2004 | Subramanyan et al. |
| 2004/0216244 A1 | 11/2004 | Cotteret et al. |
| 2004/0228580 A1 | 11/2004 | Lee et al. |
| 2004/0241114 A1 | 12/2004 | Gupta |
| 2004/0256598 A1 | 12/2004 | Plos et al. |
| 2004/0258652 A1 | 12/2004 | Pascaly et al. |
| 2005/0015894 A1 | 1/2005 | Cottard et al. |
| 2005/0036970 A1 | 2/2005 | Sabbagh et al. |
| 2005/0087718 A1 | 4/2005 | Okada |
| 2005/0095215 A1 | 5/2005 | Popp |
| 2005/0176615 A1 | 8/2005 | Kinoshita et al. |
| 2005/0186164 A1 | 8/2005 | Akyuz |
| 2005/0191263 A1 | 9/2005 | Ueyama et al. |
| 2005/0193501 A1 | 9/2005 | Chan et al. |
| 2005/0201966 A1 | 9/2005 | Ueyama et al. |
| 2006/0024257 A1 | 2/2006 | Chang et al. |
| 2006/0062751 A1 | 3/2006 | Sato et al. |
| 2006/0075580 A1 | 4/2006 | Chan et al. |
| 2006/0093571 A1 | 5/2006 | Glinski |
| 2006/0135397 A1 | 6/2006 | Bissey-Beugras et al. |
| 2006/0166845 A1 | 7/2006 | Terada |
| 2006/0182702 A1 | 8/2006 | Kitabata et al. |
| 2006/0198807 A1 | 9/2006 | Morioka |
| 2006/0228316 A1 | 10/2006 | Cannell et al. |
| 2006/0251673 A1 | 11/2006 | Hwang et al. |
| 2006/0276369 A1 | 12/2006 | Levecke et al. |
| 2007/0041921 A1 | 2/2007 | Neill et al. |
| 2007/0067924 A1 | 3/2007 | Beck et al. |
| 2007/0107142 A1 | 5/2007 | Nguyen et al. |
| 2007/0116661 A1 | 5/2007 | Mata |
| 2007/0160560 A1 | 7/2007 | Laurent et al. |
| 2007/0161543 A1 | 7/2007 | Yu et al. |
| 2007/0190008 A1 | 8/2007 | Campain et al. |
| 2007/0261594 A1 | 11/2007 | Vaskelis et al. |
| 2007/0264208 A1 | 11/2007 | Mougin et al. |
| 2008/0025937 A1 | 1/2008 | Cassier |
| 2008/0025939 A1 | 1/2008 | Cassier et al. |
| 2008/0066773 A1 | 3/2008 | Anderson et al. |
| 2008/0118458 A1 | 5/2008 | Giesen et al. |
| 2008/0124295 A1 | 5/2008 | Duranton et al. |
| 2008/0138309 A1 | 6/2008 | Malle et al. |
| 2008/0141468 A1 | 6/2008 | Cotteret |
| 2008/0187506 A1 | 8/2008 | Carballada et al. |
| 2008/0226576 A1 | 9/2008 | Benabdillah et al. |
| 2008/0233072 A1 | 9/2008 | Bureiko et al. |
| 2008/0306025 A1 | 12/2008 | Yu et al. |
| 2009/0022681 A1 | 1/2009 | Carballada et al. |
| 2009/0041699 A1* | 2/2009 | Molenda .............. A61K 8/891 424/70.1 |
| 2009/0053165 A1 | 2/2009 | Brown et al. |
| 2009/0071493 A1 | 3/2009 | Nguyen et al. |
| 2009/0074683 A1 | 3/2009 | Nguyen et al. |
| 2009/0126756 A1 | 5/2009 | Syed et al. |
| 2009/0208499 A1 | 8/2009 | Yu et al. |
| 2009/0214628 A1 | 8/2009 | de Rijk |
| 2009/0252697 A1 | 10/2009 | Barbarat et al. |
| 2009/0274677 A1 | 11/2009 | Isaacs et al. |
| 2010/0004391 A1 | 1/2010 | Haddleton et al. |
| 2010/0015079 A1 | 1/2010 | Schrader |
| 2010/0081716 A1 | 4/2010 | Matsunaga et al. |
| 2010/0119468 A1 | 5/2010 | Garcia Castro et al. |
| 2010/0154140 A1 | 6/2010 | Simonet et al. |
| 2010/0158845 A1 | 6/2010 | Ellington et al. |
| 2010/0158964 A1 | 6/2010 | Cunningham et al. |
| 2010/0178267 A1 | 7/2010 | Puerta et al. |
| 2010/0189795 A1 | 7/2010 | Dreher |
| 2010/0202998 A1 | 8/2010 | Ramos-Stanbury et al. |
| 2010/0247463 A1 | 9/2010 | Yu et al. |
| 2010/0303748 A1 | 12/2010 | Hercouet |
| 2011/0056508 A1 | 3/2011 | Gross et al. |
| 2011/0061671 A1 | 3/2011 | Neplaz et al. |
| 2011/0142778 A1 | 6/2011 | Hloucha et al. |
| 2011/0150804 A1 | 6/2011 | Nojiri et al. |
| 2011/0213033 A1 | 9/2011 | Tokuyama et al. |
| 2011/0256084 A1 | 10/2011 | Dixon et al. |
| 2011/0311463 A1 | 12/2011 | Diamond et al. |
| 2012/0015894 A1 | 1/2012 | Terada |
| 2012/0022037 A1 | 1/2012 | Terada |
| 2012/0064137 A1 | 3/2012 | Kawai |
| 2012/0114583 A1 | 5/2012 | Giesen et al. |
| 2012/0118316 A1 | 5/2012 | Uellner et al. |
| 2012/0121706 A1 | 5/2012 | Paus et al. |
| 2012/0180807 A1 | 7/2012 | Flohr |
| 2012/0230935 A1 | 9/2012 | Kim et al. |
| 2012/0244082 A1 | 9/2012 | Sulzbach et al. |
| 2012/0288459 A1 | 11/2012 | Burg et al. |
| 2012/0329650 A1 | 12/2012 | Lopez-Cervantes |
| 2013/0016246 A1 | 1/2013 | Hatanaka et al. |
| 2013/0034515 A1 | 2/2013 | Stone et al. |
| 2013/0102513 A1 | 4/2013 | Terada |
| 2013/0118996 A1 | 5/2013 | Kaplan |
| 2013/0149274 A1 | 6/2013 | Nguyen et al. |
| 2013/0152959 A1 | 6/2013 | Genain et al. |
| 2013/0156716 A1 | 6/2013 | Yontz |
| 2013/0164240 A1 | 6/2013 | Schrott |
| 2013/0172518 A1 | 7/2013 | Huang et al. |
| 2013/0216491 A1 | 8/2013 | Ogihara et al. |
| 2013/0233331 A1 | 9/2013 | Khenniche et al. |
| 2013/0233332 A1 | 9/2013 | Khenniche et al. |
| 2013/0266529 A1 | 10/2013 | Deconinck et al. |
| 2013/0280199 A1 | 10/2013 | Albert et al. |
| 2013/0309190 A1 | 11/2013 | Dimotakis et al. |
| 2013/0315852 A1 | 11/2013 | Streuli |
| 2014/0120047 A1 | 5/2014 | Krueger |
| 2014/0158150 A1 | 6/2014 | Schoepgens et al. |
| 2014/0170105 A1 | 6/2014 | Chen et al. |
| 2014/0171354 A1 | 6/2014 | Miralles et al. |
| 2014/0186283 A1 | 7/2014 | Cabourg et al. |
| 2014/0196741 A1 | 7/2014 | Cabourg et al. |
| 2014/0246041 A1 | 9/2014 | Krueger |
| 2014/0256885 A1 | 9/2014 | Puerta et al. |
| 2015/0004117 A1 | 1/2015 | Tan et al. |
| 2015/0004119 A1 | 1/2015 | Tan et al. |
| 2015/0034117 A1 | 2/2015 | Pressly et al. |
| 2015/0034119 A1 | 2/2015 | Pressly et al. |
| 2015/0037270 A1 | 2/2015 | Pressly et al. |
| 2015/0037271 A1 | 2/2015 | Pressly et al. |
| 2015/0053228 A1 | 2/2015 | Bonauer et al. |
| 2015/0053230 A1 | 2/2015 | Myatt |
| 2015/0090285 A1 | 4/2015 | Worner et al. |
| 2015/0157544 A1 | 6/2015 | Briggs et al. |
| 2015/0252302 A1 | 9/2015 | Rieth et al. |
| 2015/0283041 A1 | 10/2015 | Benn et al. |
| 2015/0290101 A1 | 10/2015 | Pressly et al. |
| 2015/0297496 A1 | 10/2015 | Kroon et al. |
| 2015/0313816 A1 | 11/2015 | Daubresse |
| 2015/0328102 A1 | 11/2015 | Pressly et al. |
| 2016/0058688 A1 | 3/2016 | Anderheggen et al. |
| 2016/0081899 A1 | 3/2016 | Pressly et al. |
| 2016/0166479 A1* | 6/2016 | Chiou .................... A61K 8/585 514/785 |
| 2016/0175238 A1 | 6/2016 | Shin et al. |
| 2016/0193129 A1 | 7/2016 | Pressly et al. |
| 2016/0235649 A1 | 8/2016 | Streuli |
| 2016/0263003 A1 | 9/2016 | Pressly et al. |
| 2016/0310394 A1 | 10/2016 | Pressly et al. |
| 2016/0331664 A1 | 11/2016 | Anderheggen et al. |
| 2016/0348037 A1 | 12/2016 | Findlay et al. |
| 2017/0007518 A1 | 1/2017 | Everaert et al. |
| 2017/0112740 A1 | 4/2017 | Schoepgens et al. |
| 2017/0112743 A1 | 4/2017 | Schoepgens et al. |
| 2017/0113071 A1 | 4/2017 | Schoepgens et al. |
| 2017/0119122 A1 | 5/2017 | Rautenberg-Groth et al. |
| 2017/0128334 A1 | 5/2017 | Schoepgens et al. |
| 2017/0128342 A1 | 5/2017 | Schoepgens et al. |
| 2017/0143611 A1 | 5/2017 | Hippe et al. |

(56) References Cited

U.S. PATENT DOCUMENTS

| | | | |
|---|---|---|---|
| 2017/0151143 A1 | 6/2017 | Scheunemann et al. | |
| 2017/0151144 A1 | 6/2017 | Scheunemann et al. | |
| 2017/0151146 A1 | 6/2017 | Scheunemann et al. | |
| 2017/0151147 A1 | 6/2017 | Scheunemann et al. | |
| 2017/0151156 A1 | 6/2017 | Scheunemann et al. | |
| 2017/0157011 A1 | 6/2017 | Punyani et al. | |
| 2017/0165161 A1 | 6/2017 | Manneck et al. | |
| 2017/0202763 A1 | 7/2017 | Manneck et al. | |
| 2017/0246094 A1* | 8/2017 | Dreher | A61Q 5/08 |
| 2017/0252291 A1 | 9/2017 | Lechner et al. | |
| 2017/0360658 A1 | 12/2017 | Ferrari et al. | |
| 2018/0055751 A1 | 3/2018 | Gevgilili et al. | |
| 2018/0116942 A1 | 5/2018 | Mahadeshwar et al. | |
| 2018/0140531 A1 | 5/2018 | Singer et al. | |
| 2018/0140532 A1 | 5/2018 | Singer et al. | |
| 2018/0280267 A1 | 10/2018 | Rughani et al. | |
| 2018/0280269 A1 | 10/2018 | Rughani et al. | |
| 2018/0280270 A1 | 10/2018 | Rughani et al. | |
| 2018/0280271 A1 | 10/2018 | Fack et al. | |
| 2018/0338895 A1 | 11/2018 | Patterson et al. | |
| 2018/0338901 A1 | 11/2018 | Patterson et al. | |
| 2018/0339175 A1 | 11/2018 | Patterson et al. | |
| 2019/0160000 A1* | 5/2019 | Herrlein | A61Q 5/065 |
| 2019/0201309 A1 | 7/2019 | Machover et al. | |
| 2020/0129405 A1 | 4/2020 | Mitchell et al. | |

FOREIGN PATENT DOCUMENTS

| | | |
|---|---|---|
| CN | 1424016 A | 6/2003 |
| CN | 1454074 A | 11/2003 |
| CN | 1678281 A | 10/2005 |
| CN | 1717215 A | 1/2006 |
| CN | 1778289 A | 5/2006 |
| CN | 1798539 A | 7/2006 |
| CN | 101282705 A | 10/2008 |
| CN | 101495087 A | 7/2009 |
| CN | 101686920 A | 3/2010 |
| CN | 101843561 A | 9/2010 |
| CN | 101966136 A | 2/2011 |
| CN | 102056896 A | 5/2011 |
| CN | 102166163 A | 8/2011 |
| CN | 102231974 A | 11/2011 |
| CN | 102281864 A | 12/2011 |
| CN | 102361627 A | 2/2012 |
| CN | 102397232 A | 4/2012 |
| CN | 102451117 A | 5/2012 |
| CN | 103356395 A | 10/2013 |
| CN | 103998099 A | 8/2014 |
| CN | 104066419 A | 9/2014 |
| CN | 104159567 A | 11/2014 |
| CN | 104519962 A | 4/2015 |
| CN | 105267066 A | 1/2016 |
| CN | 105902403 A | 8/2016 |
| CN | 105902404 A | 8/2016 |
| CN | 106265109 A | 1/2017 |
| DE | 1220969 B | 7/1966 |
| DE | 2225541 A1 | 12/1973 |
| DE | 2359399 A1 | 6/1975 |
| DE | 3843892 A1 | 6/1990 |
| DE | 4133957 A1 | 4/1993 |
| DE | 4300320 A1 | 7/1994 |
| DE | 19543988 A1 | 5/1997 |
| DE | 10051773 A1 | 4/2002 |
| DE | 10051774 A1 | 4/2002 |
| DE | 20208254 U1 | 8/2002 |
| DE | 102004052480 A1 | 5/2006 |
| DE | 10 2007 039745 A1 | 2/2009 |
| DE | 202015104742 U1 | 10/2015 |
| DE | 102014213317 A1 | 1/2016 |
| DE | 102015223828 A1 | 9/2016 |
| DE | 102015221460 A1 | 5/2017 |
| DE | 102016200688 A1 | 7/2017 |
| DE | 202017001430 | 7/2017 |
| EP | 0122324 A1 | 10/1984 |
| EP | 0159628 A2 | 10/1985 |
| EP | 0286261 A2 | 10/1988 |
| EP | 0298684 A2 | 1/1989 |
| EP | 0299764 A2 | 1/1989 |
| EP | 0437114 A1 | 7/1991 |
| EP | 0512879 A2 | 11/1992 |
| EP | 0636358 A1 | 2/1995 |
| EP | 0714954 A2 | 6/1996 |
| EP | 0770375 A1 | 5/1997 |
| EP | 0855178 A2 | 7/1998 |
| EP | 0978272 A1 | 2/2000 |
| EP | 1118319 A1 | 7/2001 |
| EP | 1174112 A2 | 1/2002 |
| EP | 1216023 B1 | 4/2005 |
| EP | 1541117 A1 | 6/2005 |
| EP | 1570832 A1 | 9/2005 |
| EP | 1216022 B1 | 4/2006 |
| EP | 1690524 A2 | 8/2006 |
| EP | 1779896 A2 | 5/2007 |
| EP | 1810657 A1 | 7/2007 |
| EP | 2123250 A1 | 11/2009 |
| EP | 2165697 A1 | 3/2010 |
| EP | 2229933 A1 | 9/2010 |
| EP | 2295029 A1 | 3/2011 |
| EP | 2460511 A1 | 6/2012 |
| EP | 2471504 A1 | 7/2012 |
| EP | 2478892 A1 | 7/2012 |
| EP | 1510197 B1 | 3/2016 |
| FR | 1492597 A | 8/1967 |
| FR | 1583363 A | 10/1969 |
| FR | 2162025 A | 7/1973 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2413907 A1 | 8/1979 |
| FR | 2505348 A1 | 11/1982 |
| FR | 2542997 A1 | 9/1984 |
| FR | 2733749 A1 | 11/1996 |
| FR | 2789895 A1 | 8/2000 |
| FR | 2789896 A1 | 8/2000 |
| FR | 2801308 A1 | 5/2001 |
| FR | 2841129 A1 | 12/2003 |
| FR | 2886136 A1 | 12/2006 |
| FR | 2939030 A1 | 6/2010 |
| FR | 2944441 A1 | 10/2010 |
| FR | 2966352 A1 | 4/2012 |
| FR | 2975899 A1 | 12/2012 |
| FR | 2975900 A1 | 12/2012 |
| GB | 713675 A | 8/1954 |
| GB | 741307 A | 11/1955 |
| GB | 773559 A | 4/1957 |
| GB | 1026978 A | 4/1966 |
| GB | 1125794 A | 8/1968 |
| GB | 1153196 A | 5/1969 |
| GB | 1260451 A | 1/1972 |
| GB | 1546809 A | 5/1979 |
| GB | 1584364 A | 2/1981 |
| JP | 63-154611 A | 6/1988 |
| JP | S63-255214 A | 10/1988 |
| JP | 02-019576 A | 1/1990 |
| JP | H02-138110 A | 5/1990 |
| JP | 05-163124 A | 6/1993 |
| JP | H07-069847 A | 3/1995 |
| JP | 08-198732 A | 8/1996 |
| JP | H08-509478 A | 10/1996 |
| JP | 2000-229821 A | 8/2000 |
| JP | 2001-081013 A | 3/2001 |
| JP | 2002-097115 A | 4/2002 |
| JP | 2002-105493 A | 4/2002 |
| JP | 2002-121121 A | 4/2002 |
| JP | 2002-356408 A | 12/2002 |
| JP | 2002-363048 A | 12/2002 |
| JP | 2003-095876 A | 4/2003 |
| JP | 2003-516335 A | 5/2003 |
| JP | 2004-026976 A | 1/2004 |
| JP | 2005-060398 A | 3/2005 |

(56) References Cited

FOREIGN PATENT DOCUMENTS

| | | |
|---|---|---|
| JP | 2005-154348 A | 6/2005 |
| JP | 2006-2194593 A | 8/2006 |
| JP | 2006-327994 A | 12/2006 |
| JP | 2008-189686 A | 8/2008 |
| JP | 2009-007283 A | 1/2009 |
| JP | 2009-536619 A | 10/2009 |
| JP | 2010-155823 A | 7/2010 |
| JP | 2012-515218 A | 7/2012 |
| JP | 2013-500328 A | 1/2013 |
| JP | 2015-086211 A | 5/2015 |
| JP | 2016-003185 A | 1/2016 |
| JP | 2017-095451 A | 6/2017 |
| JP | 2018-514570 A | 6/2018 |
| KR | 10-2001-0039848 A | 7/2001 |
| KR | 2003-0003970 A | 1/2003 |
| KR | 10-2004-0098688 A | 11/2004 |
| KR | 10-2006-0059564 A | 6/2006 |
| KR | 10-2012-0062511 A | 6/2012 |
| KR | 10-2016-0064420 A | 6/2016 |
| RU | 2144945 C1 | 1/2000 |
| RU | 2229281 C1 | 5/2004 |
| WO | 93/00882 A1 | 1/1993 |
| WO | 93/08787 A2 | 5/1993 |
| WO | 94/08969 A1 | 4/1994 |
| WO | 94/08970 A1 | 4/1994 |
| WO | 95/01152 A1 | 1/1995 |
| WO | 95/01772 A1 | 1/1995 |
| WO | 95/15144 A1 | 6/1995 |
| WO | 96/15765 A1 | 5/1996 |
| WO | 97/24106 A1 | 7/1997 |
| WO | 98/56333 A1 | 12/1998 |
| WO | 99/11226 A1 | 3/1999 |
| WO | 99/66793 A1 | 12/1999 |
| WO | 01/35912 A1 | 5/2001 |
| WO | 01/47486 A1 | 7/2001 |
| WO | 01/52005 A1 | 7/2001 |
| WO | 02/19976 A1 | 3/2002 |
| WO | 02/32383 A2 | 4/2002 |
| WO | 02/32386 A2 | 4/2002 |
| WO | 02/055034 A2 | 7/2002 |
| WO | 2004/002411 A2 | 1/2004 |
| WO | 2004/019858 A2 | 3/2004 |
| WO | 2016/058749 A1 | 4/2005 |
| WO | 2005/058258 A1 | 6/2005 |
| WO | 2006/011771 A1 | 2/2006 |
| WO | 2006/134051 A1 | 12/2006 |
| WO | 2007/003307 A1 | 1/2007 |
| WO | 2007/038733 A1 | 4/2007 |
| WO | 2009/024936 A2 | 2/2009 |
| WO | 2010/015517 A2 | 2/2010 |
| WO | 2010/023559 A2 | 3/2010 |
| WO | 2010/049434 A2 | 5/2010 |
| WO | 2011/134785 A2 | 11/2011 |
| WO | 2012/033813 A2 | 3/2012 |
| WO | 2012/080321 A2 | 6/2012 |
| WO | 2012/084532 A2 | 6/2012 |
| WO | 2012/084876 A2 | 6/2012 |
| WO | 2012/164064 A1 | 12/2012 |
| WO | 2013/092080 A1 | 6/2013 |
| WO | 2013/136480 A1 | 9/2013 |
| WO | 2014/016407 A1 | 1/2014 |
| WO | 2014/072490 A1 | 5/2014 |
| WO | 2014/118212 A1 | 8/2014 |
| WO | 2014/125452 A1 | 8/2014 |
| WO | 2014/144076 A1 | 9/2014 |
| WO | 2014/167508 A1 | 10/2014 |
| WO | 2014/207097 A1 | 12/2014 |
| WO | 2015/017768 A1 | 2/2015 |
| WO | 2015/026994 A1 | 2/2015 |
| WO | 2015/033351 A1 | 3/2015 |
| WO | 2015/058942 A1 | 4/2015 |
| WO | 2015/069823 A1 | 5/2015 |
| WO | 2015/075064 A2 | 5/2015 |
| WO | 2015/118357 A2 | 8/2015 |
| WO | 2015/175986 A2 | 11/2015 |
| WO | 2016/005114 A1 | 1/2016 |
| WO | 2016/005144 A1 | 1/2016 |
| WO | 2016/069877 A1 | 5/2016 |
| WO | 2016/091492 A1 | 6/2016 |
| WO | 2016/098870 A1 | 6/2016 |
| WO | 2016/100885 A1 | 6/2016 |
| WO | 2016/102543 A1 | 6/2016 |
| WO | 2016/120642 A1 | 8/2016 |
| WO | 2016/161360 A1 | 10/2016 |
| WO | 2016/179017 A1 | 11/2016 |
| WO | 2016/198203 A1 | 12/2016 |
| WO | 2017/041903 A1 | 3/2017 |
| WO | 2017/041905 A1 | 3/2017 |
| WO | 2017/041906 A1 | 3/2017 |
| WO | 2017/041907 A1 | 3/2017 |
| WO | 2017/041908 A1 | 3/2017 |
| WO | 2017/041909 A1 | 3/2017 |
| WO | 2017/041910 A1 | 3/2017 |
| WO | 2017/059646 A1 | 4/2017 |
| WO | 2017/085117 A1 | 5/2017 |
| WO | 2017/091794 A1 | 6/2017 |
| WO | 2017/091796 A1 | 6/2017 |
| WO | 2017/091797 A1 | 6/2017 |
| WO | 2017/091800 A1 | 6/2017 |
| WO | 2017/102855 A1 | 6/2017 |
| WO | 2017/102936 A1 | 6/2017 |
| WO | 2017/116465 A1 | 7/2017 |
| WO | 2017/196299 A1 | 11/2017 |
| WO | 2017/207198 A1 | 12/2017 |
| WO | 2018/081399 A1 | 5/2018 |
| WO | 2018/085478 A1 | 5/2018 |

OTHER PUBLICATIONS

Third Party Submission for U.S. Appl. No. 16/712,326 with attachments, filed Sep. 8, 2020.
Mexican Office Action for counterpart Application No. MX/a/2017/013983, dated Sep. 15, 2020.
Non-Final Office Action for copending U.S. Appl. No. 15/778,807, dated Oct. 9, 2020.
Japanese Notice of Reasons for Refusal for counterpart Application No. 2019-553190, dated Oct. 27, 2020.
Translation of Korean Notice of Last Preliminary Rejection for counterpart Application No. 10-2018-7017668, dated Oct. 21, 2020.
Non-Final Office Action for copending U.S. Appl. No. 15/942,042, dated Nov. 12, 2020.
Final Office Action for copending U.S. Appl. No. 15/356,967, dated Nov. 17, 2020.
Final Office Action for copending U.S. Appl. No. 15/357,056, dated Nov. 19, 2020.
Japanese Office Action for counterpart Application No. 2018-546408, dated Dec. 7, 2020.
Japanese Notice of Reasons for Rejection of counterpart Application No. 2019-553559, dated Dec. 1, 2020.
Japanese Notice of Reasons for Rejection for counterpart Application No. 2019-564945, dated Dec. 1, 2020.
Mintel: "Conditioner," Unilever, XP055576893, Database accession No. 3014885, Mar. 2, 2015.
"Olaplex Alleges Patent Infringement by L'OREAL re Hairbond-Building Prior to Colouring," Focus on Pigments, vol. 2017, No. 3, Mar. 31, 2017, p. 7.
Final Office Action for copending U.S. Appl. No. 15/339,035, dated May 2, 2019.
International Preliminary Report on Patentability for counterpart Application No. PCT/US2017/058495, dated May 9, 2019.
Notice of Allowance for copending U.S. Appl. No. 15/778,803, dated Jun. 3, 2019.
Extended European Search Report for counterpart Application No. 16869327.3-1114, dated Jun. 4, 2019.
Mintel: "Detox 7 Day Cure Purifying Serum," XP055593471, Jeanne Gatineau, Feb. 11, 2013.
Extended European Search Report for counterpart Application No. 16869330.7-1114, dated Jul. 5, 2019.
Extended European Search Report for counterpart Application No. 16869326.5-1114, dated Jun. 26, 2019.

(56) References Cited

OTHER PUBLICATIONS

Translation of Mexican Office Action for counterpart Application No. MX/a/2018/005829, dated Jun. 13, 2019.
Non-Final Office Action for copending U.S. Appl. No. 15/339,035, dated Aug. 20, 2019.
Mexican Office Action for counterpart Application No. MX/a/2017/013983, dated Jul. 2, 2019.
Notice of Allowance for copending U.S. Appl. No. 16/042,478, dated Sep. 25, 2019.
Non-Final Office Action for copending U.S. Appl. No. 15/778,807, dated Sep. 30, 2019.
Brazilian Office Action for counterpart Application No. BR112017023380-0, dated Oct. 10, 2019.
Brazilian Office Action for counterpart Application No. BR112018010381-0, dated Nov. 25, 2019.
Brazilian Office Action for counterpart Application No. BR112018010357-8, dated Nov. 25, 2019.
Mexican Office Action for counterpart Application No. MX/a/2018/005829, dated Oct. 5, 2019.
Brazilian Office Action for counterpart Application No. BR112018010344, dated Nov. 25, 2019.
Mexican Office Action for counterpart Application No. MX/a/2017/013983, dated Dec. 16, 2019.
Japanese Office Action for counterpart Application No. 2018-526844, dated Dec. 23, 2019.
Japanese Office Action for counterpart Application No. 2018-526845, dated Dec. 23, 2019.
Japanese Office Action for counterpart Application No. 2018-546409, dated Dec. 23, 2019.
Brazilian Written Opinion for counterpart Application No. BR112018010341, dated Nov. 25, 2019.
Non-Final Office Action for counterpart Japanese Application No. 2018-546408, dated Jan. 6, 2020.
Mintel: "Tonic," Dr. Kurt Wolff, Dr. Wolff Plantur 39, ID# 3133037, Apr. 2015.
Mintel: "Conditioner," LG Household & Health Care, Beyond Professional, ID# 3240637, Jun. 2015.
Russian Office Action for counterpart Application No. 2018114758/04, dated Dec. 13, 2019.
Translated Notification of Reasons for Refusal for counterpart KR Application No. 10-2018-7017668, dated Jan. 21, 2020.
Translated Office Action for counterpart RU Application No. 2017134681/04(0060925), dated Dec. 30, 2019.
Non-Final Office Action for copending U.S. Appl. No. 15/778,805, dated Feb. 12, 2020.
Final Office Action for copending U.S. Appl. No. 15/778,807, dated Mar. 13, 2020.
Final Office Action for copending U.S. Appl. No. 15/339,035, dated Apr. 10, 2020.
Non-Final Office Action for copending U.S. Appl. No. 16/273,787, dated Apr. 9, 2020.
International Search Report and Written Opinion for counterpart Application No. PCT/US2017/059827, dated Jun. 28, 2018.
"Lamesoft® PO 65 Datasheet," Retrieved from the internet on Jun. 7, 2018, http://e-applications.basf-ag.de/data/basf-pcan/pds2/pds2-web.nsf.
Non-Final Office Action for copending U.S. Appl. No. 15/356,967, dated May 3, 2017.
Final Office Action for copending U.S. Appl. No. 15/356,967, dated Dec. 4, 2017.
Non-Final Office Action for copending U.S. Appl. No. 15/356,967, dated Aug. 24, 2018.
Final Office Action for copending U.S. Appl. No. 15/356,967, dated Apr. 11, 2019.
Non-Final Office Action for copending U.S. Appl. No. 15/356,967, dated Feb. 21, 2020.
Notice of Allowance for copending U.S. Appl. No. 15/604,152, dated Oct. 2, 2019 (now U.S. Pat. No. 10,561,599).
Non-Final Office Action for copending U.S. Appl. No. 15/604,152, dated Jun. 13, 2019.

Non-Final Office Action for copending U.S. Appl. No. 15/942,042, dated Jan. 24, 2020.
ALS "Cocamidopropyl betaine," printed 2020; http://www.caslab.com/Cocamidopropyl_betaine_CAS_61789-40-0.
Notice of Allowability for copending U.S. Appl. No. 15/604,152, dated Dec. 10, 2019.
International Search Report and Written Opinion for counterpart Application No. PCT/US2018/025466, dated Jul. 9, 2018.
International Preliminary Report on Patentability for counterpart Application No. PCT/US2018/025466, dated Oct. 1, 2019.
Corrected Notice of Allowability for copending U.S. Appl. No. 15/604,189, dated Dec. 11, 2019 (now U.S. Pat. No. 10,576,307).
Notice of Allowance for copending U.S. Appl. No. 15/604,189, dated Oct. 22, 2019.
Copending U.S. Appl. No. 15/484,625, filed Apr. 11, 2017 (WO 2016/179017).
Copending U.S. Appl. No. 15/484,663, filed Apr. 11, 2017 (WO 2017/091794).
Copending U.S. Appl. No. 15/339,035, filed Oct. 31, 2016 (WO 2018/081399).
International Search Report and Written Opinion for counterpart Application No. PCT/US2016/030172, dated Sep. 19, 2016.
International Search Report and Written Opinion for counterpart Application No. PCT/US2016/063724, dated Feb. 2, 2017.
International Search Report and Written Opinion for counterpart Application No. PCT/US2016/063727, dated Feb. 8, 2017.
International Search Report and Written Opinion for counterpart Application No. PCT/US2016/063732, dated Feb. 6, 2017.
International Search Report and Written Opinion for counterpart Application No. PCT/US2016/063728, dated Feb. 1, 2017.
Mintel: "Abundant Volume Conditioner," Alterna Professional Haircare, Database Record No. 2177147, Sep. 2013.
Mintel: "Hair Colourant," Catzy Hair Colourant, Database Record ID 743114, Jul. 2007, 4 pages.
Mintel: "Combing Cream," Devintex Cosmeticos, Database Record No. 1595490, Jul. 2011.
Mintel: "Combing Cream," Devintex Cosmeticos, Database Record No. 1595658, Jul. 2011.
Mintel: "Conditioner," Devintex Cosmeticos, Database Record No. 1595545, Jul. 2011.
Mintel: "Conditioner," Laperle Haircare, Database Record No. 3645337, Feb. 2016.
Mintel: "Conditioner," Laperle Haircare, Database Record No. 3790215, Feb. 2016.
Mintel: "Conditioner," Liqwd, Database Record No. 1172691, Sep. 2009.
Mintel: "Conditioner," TIGI, Database Record No. 1442418, Nov. 2010.
Mintel: "Conditioner," TIGI International, Database Record No. 1445427, Nov. 2010.
Mintel: "Conditioner," TGI International, Database Record No. 3280151, Jul. 2015.
Mintel, "Masque for Beautiful Color," Oribe Hair Care, Database Record No. 1522953, Mar. 2011.
Mintel: "Moisturizing Conditioner," Frederic Fekkai, Database Record No. 1507159, Mar. 2011.
Mintel: "Post-Service Perfector," Redken, Database Record No. 4326453, Nov. 2016.
Mintel: "Step 3-Conditioner," L'OREAL, Database Record No. 4353779, Oct. 2016.
Mintel: "Step 3-Conditioner," L'OREAL, Database Record No. 4609117, Feb. 2017.
International Preliminary Report on Patentability for counterpart Application No. PCT/US2016/30172, dated Jun. 19, 2017.
Petition for Post-Grant Review of U.S. Pat. No. 9,498,419, filed Jan. 31, 2017, with Exhibits.
Non-Final Office Action for copending U.S. Appl. No. 15/484,625, dated Jun. 21, 2017 (now U.S. Pat. No. 10,231,915).
Final Office Action for copending U.S. Appl. No. 15/484,625, dated Nov. 14, 2017 (now U.S. Pat. No. 10,231,915).
Non-Final Office Action for copending U.S. Appl. No. 15/484,663, dated Jun. 21, 2017 (now U.S. Pat. No. 10,058,494).

(56) References Cited

OTHER PUBLICATIONS

Final Office Action for copending U.S. Appl. No. 15/484,663, dated Nov. 28, 2017 (now U.S. Pat. No. 10,058,494).
Non-Final Office Action for copending U.S. Appl. No. 15/339,035, dated Jan. 10, 2018.
International Search Report for counterpart Application No. PCT/US2017/058495, dated Jan. 5, 2018.
Third Party Submission for U.S. Appl. No. 15/484,663, filed Feb. 28, 2018, with attachments.
Pressly, Eric et al., U.S. Appl. No. 61/994,709, filed May 16, 2014 and became publicly available on Nov. 19, 2015.
Estetica: the hairstyling professional magazine, (http://estetica.it/int/a/schwarzkopf-professional-launches-fibreplex), "Schwarzkopf Professional Launches Fibreplex®," published Sep. 23, 2015 reporting that Fibreplex was launched during Sep. 2015.
Fibreplex® No. 1 Product Label.
Fibreplex® No. 1 Material Safety Data Sheet.
International Preliminary Report on Patentability for counterpart Application No. PCT/US2016/063727, dated Jun. 7, 2018.
International Preliminary Report on Patentability for counterpart Application No. PCT/US2016/063732, dated Jun. 7, 2018.
International Preliminary Report on Patentability for counterpart Application No. PCT/US2016/063728, dated Jun. 7, 2018.
Non-Final Office Action for copending U.S. Appl. No. 15/484,625, dated Jun. 20, 2018 (now U.S. Pat. No. 10,231,915).
International Preliminary Report on Patentability for counterpart Application No. PCT/US2016/063724, dated Jun. 7, 2018.
Non-Final Office Action for copending U.S. Appl. No. 15/339,035, dated Oct. 5, 2018.
Notice of Allowance for copending U.S. Appl. No. 15/484,625, dated Oct. 31, 2018.
Bayraktar, V.N., "Organic Acids Concentration in Wine Stocks After *Saccharomyces cerevisiae* Fermentation," Biotechnologia Acta, vol. 6, No. 2, Jan. 1, 2013, pp. 97-106.
Supplementary European Search Report for counterpart Application No. EP16789846, dated Oct. 30, 2018.
Communication Pursuant to Rules 70(32) and 70a(2) EC for counterpart Application EP16789846, dated Jan. 23, 2019.
Written Opinion for counterpart Application EP16789846, dated Jan. 23, 2019.
Supplementary Extended Search Report and Written Opinion for counterpart European Application No. 16869324, dated Apr. 25, 2019.
Mintel: "Conditioner," Unilever, XP-55576888, Database accession No. 1419415, Oct. 21, 2010.
Non-Final Office Action for copending U.S. Appl. No. 15/604,189, dated Apr. 8, 2019.
International Search Report and Written Opinion for counterpart Application No. PCT/US2018/034371, dated Nov. 16, 2018.
Mintel: "Hydrating Hair Colour," Garnier, Jan. 2017, pp. 1-6.
Final Office Action for copending U.S. Appl. No. 15/603,889, dated Jul. 12, 2019.
Non-Final Office Action for copending U.S. Appl. No. 15/603,889, dated Jan. 2, 2019.
International Search Report and Written Opinion for counterpart Application No. PCT/US2018/034378, dated Jul. 24, 2018.
Final Office Action for copending U.S. Appl. No. 16/234,883, dated Mar. 11, 2020.
Final Office Action for copending U.S. Appl. No. 16/176,350, dated Apr. 8, 2020.
Non-Final Office Action for copending U.S. Appl. No. 16/176,350, dated Nov. 14, 2019.
International Search Report and Written Opinion for counterpart Application No. PCT/US2019/059002, dated Feb. 4, 2020.
Korean Notification of Reasons for Refusal of counterpart Application No. KR10-2017-7034789, dated May 19, 2020.
Non-Final Office Action for copending U.S. Appl. No. 16/176,350, dated Sep. 30, 2020.
Non-Final Office Action for copending U.S. Appl. No. 16/234,883, dated Sep. 16, 2019.
International Search Report and Written Opinion for counterpart Application No. PCT/US2018/067814, dated Feb. 25, 2019.
Final Office Action for copending U.S. Appl. No. 15/942,042, dated Jun. 1, 2020.
Japanese Notice of Reasons for Refusal for Application No. 2017-557074, dated Jun. 1, 2020.
Non-Final Office Action for copending U.S. Appl. No. 15/942,085, dated Jun. 19, 2020.
Mintel, "Masque Force Architecte Reconstructing Masque," L'Oreal, Feb. 2012, pp. 1-6.
Shiseido Super Mild Hair Care—Shampoo and Conditioner Refill Set. https://web.archive.org/web/20160326190615/nttp://www.truenu.com/TR/Shiseido-Super-Mild-Hair-Care-Shampoo-Conditioner-Refill-Set-Two-400ml-Refill-Pouches-Details.html. Published Mar. 26, 2016.
Non-Final Office Action for copending U.S. Appl. No. 15/941,916, dated Jun. 24, 2020.
Non-Final Office Action for copending U.S. Appl. No. 15/941,965, dated Jul. 15, 2020.
Third Party Observation for counterpart Application No. EP20160869330, dated Jun. 26, 2020.
Third Party Observation for counterpart Application No. EP20160869326, dated Jul. 2, 2020.
Third Party Observation for counterpart Application No. EP20160869327, dated Jul. 2, 2020.
International Search Report and Written Opinion for counterpart Application No. PCT/US2018/025448, dated Jul. 9, 2018.
International Preliminary Report on Patentability for counterpart Application No. PCT/US2018/025448, dated Oct. 1, 2019.
International Search Report and Written Opinion for counterpart Application No. PCT/US2018/025431, dated Jun. 20, 2018.
International Preliminary Report on Patentability for counterpart Application No. PCT/US2018/025431, dated Oct. 1, 2019.
International Search Report and Written Opinion for counterpart Application No. PCT/US2018/025418, dated Jun. 21, 2018.
International Preliminary Report on Patentability for counterpart Application No. PCT/US2018/025418, dated Oct. 1, 2019.
Translated Japanese Office Action for counterpart Application No. 2018-526844, dated Aug. 3, 2020.
Translation of Mexican Office Action for counterpart Application No. MX/a/2018/005829, dated Jul. 13, 2020.
Non-Final Office Action for copending U.S. Appl. No. 16/234,883 dated Aug. 26, 2020.
Mascolo Group, label.m Anti-Frizz Mist, Mintel Gnpd, record ID5618119, published Apr. 2018, p. 1-5.
Federici Brands, Color WOW Dream Coat Supernatural Spray, Mintel GNPD, record ID5637153, published Apr. 2018, p. 1-2.
Garnier, Garnier Fructis Sleek & Shine Moroccan Sleek Oil Treatment, Mintel GNPD, record ID1876023, published Sep. 2012, p. 1-2.
Duai, Leave-In Conditioner, Mintel GNPD, record ID5781323, published Jun. 2018, p. 1-2.
Redken, Redken Pillow Proof Express Treatment Primer, Mintel Gnpd, record ID5117339, published Sep. 2017, p. 1-4.
Redken, Redken Pillow Proof Express Primer Time-Saving Blowdry Primer with Heat Protection, Mintel GNPD, record ID6117357, published Nov. 2018, p. 1-2.
Redken, Redken Pillow Proof Time-Saving Blowdry Primer with Heat Protection, Mintel GNPD, record ID4537755, published Jan. 2017, p. 1-3.
International Search Report and Written Opinion for counterpart Application No. PCT/US2017/059817, dated Feb. 6, 2018.
Non-Final Office Action for copending U.S. Appl. No. 15/357,056, dated Apr. 16, 2020.
Olaplex with relaxers, Olaplex™, pp. 1-2, Apr. 11, 2017, https://olaplex.es/olaplex-with-relaxers/.
Relaxers, resource Library, Olaplex Education, pp. 1-2, Apr. 11, 2017, https://help.olaplex.com/detail/relaxers.
International Search Report and Written Opinion for counterpart Application No. PCT/US2018/034366, dated Jul. 25, 2018.
Anonymous: "Curly Hair Conditioner," Mintel, GNPD, XP002782449, 2015, pp. 1-2.

(56) References Cited

OTHER PUBLICATIONS

Translation of Chinese Office Action for counterpart Application No. 201680079110.9, dated Aug. 11, 2020.
Ruiming, Li, "Hairdressing Technology," China Railway Publishing House, Jun. 30, 2015, pp. 112-113.
Copending U.S. Appl. No. 16/455,139, "Hair Treatment Compositions and Methods for Treating Hair," filed Jun. 27, 2019.
Translation of Russian Office Action for counterpart Application No. 2017134681-04, dated Aug. 17, 2020.
Final Office Action for copending U.S. Appl. No. 16/234,883, dated Dec. 24, 2020.
Translation of Third Party Observation for Application No. 2018-546408, dated Sep. 11, 2020.
European Office Action for counterpart Application No. 16869327.3-1 112, dated Dec. 18, 2020.
Translation of Russian Office Action for counterpart Application No. 218114758/04, dated Dec. 21, 2020.
Final Office Action for copending U.S. Appl. No. 15/941,916, dated Mar. 10, 2021.
Final Office Action for copending U.S. Appl. No. 15/941,965, dated Apr. 5, 2021.
Translation of Chinese Office Action for counterpart Application No. 201880021603.6, dated Mar. 2, 2021.
Translation of Chinese Office Action for counterpart Application No. 201680039105.5, dated Feb. 4, 2021.
European Office Action for counterpart Application No. 16869330.7-1112, dated Feb. 4, 2021.
European Office Action for counterpart Application No. 16869324.0-1112, dated Feb. 18, 2021.
Translation of Chinese Office Action for counterpart Application No. 201680079800.4, dated Feb. 24, 2021.
Supplemental Search Report for Chinese counterpart Application No. 201680079800.4, dated Feb. 18, 2021.
Final Office Action for copending U.S. Appl. No. 15/942,042, dated May 12, 2021.
Non-Final Office Action for copending U.S. Appl. No. 15/942,085, dated Jun. 8, 2021.
Tetrasodium Etidronate, https://uk.lush.com/ingredients/tetrasodium-etidronate. Published Mar. 28, 2020.
Shoup, F.K., et al., "Amino Acid Composition of Wheat Varieties and Flours Varying Widely in Bread-Making Potentialities," Journal of Food Science, vol. 31, Issue 1, published Jan. 1966, pp. 94-101.
"Oxy Cream," Makki Cosmetics, https://www.makkicosmetics.com/makki/showProductjsp?productID=Oxy25030&brandID=Makki, published Jun. 30, 2016.
Non-Final Office Action for copending U.S. Appl. No. 15/339,035, dated Jun. 25, 2021.
Non-Final Office Action for copending U.S. Appl. No. 15/603,889, dated Jun. 25, 2021.

Partial Translation of Office Action for copending MX Application No. MX/a/2017/013983, dated Apr. 4, 2021.
Translation of Chinese Office Action for counterpart Application No. 201680079773, dated Apr. 14, 2021.
Translation of Japanese Office Action for counterpart Application No. 2017-557074, dated May 31, 2021.
Translation of Japanese Notice of Reasons for Refusal for counterpart Application No. 2019-553190, dated Jun. 12, 2021.
Non-Final Office Action for copending U.S. Appl. No. 16/234,883, dated Sep. 17, 2021.
Final Office Action for copending U.S. Appl. No. 15/942,085, dated Sep. 21, 2021.
Final Office Action for copending U.S. Appl. No. 15/778,807, dated Jul. 21, 2021.
Non-Final Office Action for copending U.S. Appl. No. 15/356,967, dated Jul. 22, 2021.
Copending U.S. Appl. No. 17/403,327, titled: "Hair Treatment Compositions, Methods, and Kits for Treating Hair," Inventors: Barbara Mitchell et al., filed Aug. 16, 2021.
Final Office Action for copending U.S. Appl. No. 15/603,889, dated Jan. 6, 2022.
Translation of Chinese Office Action for counterpart Application No. 201680039105.5, dated Jan. 14, 2022.
Translation of Chinese Office Action for counterpart Application No. 201880034056.5 dated Dec. 28, 2021.
Communication Pursuant to Rule 114(2) EPC (Third Party Observation) for EP Application No. 20160869324, dated Apr. 22, 2022.
U.S. Appl. No. 61/994,709 for "Hair Treatment Compositions and Methods," Inventors: Eric D. Pressly and Craig J. Hawker, filed May 16, 2014.
"Practical Modern Hair Science," Chapter 4, Edited by Trefor Evans and R. Randall Wickett, Allured Business Media, 2012, pp. 1065-1-1065-45.
Third Party Submission for counterpart Application No. EP 20160869330, dated May 6, 2022.
Translation of Second Chinese Office Action for counterpart Application No. 201880034056.5, dated May 30, 2022.
Chinese Office Action for counterpart Application No. 201880084390.1, dated Jun. 30, 2022 (translation unavailable).
EP Office Action for counterpart Application No. 16789846.9-1109, dated Jul. 6, 2022.
Final Office Action for copending U.S. Appl. No. 15/339,035, dated Apr. 14, 2022.
Third Party Submission and Concise Description of Relevance for U.S. Appl. No. 17/356,132, dated Apr. 20, 2022.
Third Party Submission for copending U.S. Appl. No. 17/379,405, filed May 10, 2022.
Non-Final Office Action for copending U.S. Appl. No. 15/942,042, dated May 23, 2022.
Third Party Submission and Concise Description of Relevance for copending U.S. Appl. No. 17/403,327, dated Jun. 27, 2022.

* cited by examiner

HAIR TREATMENT COMPOSITIONS AND METHODS FOR TREATING HAIR

FIELD OF THE DISCLOSURE

The instant disclosure relates to hair treatment compositions that are particularly useful for improving the quality of hair and which can impart beneficial properties such as styling, frizz control, and retention of shape/curl. Also disclosed are methods for using the hair treatment compositions.

BACKGROUND

Many consumers desire to use cosmetic and care compositions that enhance the appearance of keratinous substrates such as hair, e.g., by changing the color, style, and/or shape of the hair, and/or by imparting various cosmetic properties to hair, such as shine and conditioning. Many of the known compositions and processes for enhancing the appearance of hair involve chemical treatments to the hair.

The process of changing the color of hair, for example, can involve depositing an artificial color onto the hair which provides a different shade or color to the hair, and/or lifting the color of the hair, such as lightening the color of dark hair to lighter shades, which m requires the use of oxidizing agents.

Additionally, there are many techniques and compositions for styling or altering the shape of hair. For example, hair care products referred to as "hair relaxers" or "hair straighteners" can relax or straighten curly or kinky hair, including wavy hair. Straightening or relaxing the curls of very curly hair may increase the manageability and ease of styling of such hair. Compositions for permanent waving the hair will impart a curl or a wave to otherwise straight hair. Different types of compositions can be applied onto hair in order to change its shape and make it more manageable, such as alkaline and acidic compositions. Hair relaxers, straighteners, perms, and/or waves may either be applied in a hair salon by a professional or in the home by the individual consumer.

While dyeing or color lifting compositions can effectively alter the color of hair, and relaxing, straightening, perming, and waving compositions can effectively alter the shape of the hair, these chemical treatments can damage the hair fibers and/or irritate the scalp. Thus, in order to reduce or avoid damage to hair, as well as to improve the cosmetic performance of the compositions, different types of hair styling products have been developed by manufacturers that are aimed to help consumers achieve a desired look, including one or more of fuller hair, thicker hair, sleek and straight hair, frizz-free hair, and defined curls. These products are typically provided in forms that are applied after the shampooing and conditioning processes are completed.

In one example, styling products are available that provide protection against external factors such as protection from moisture to minimize or reduce frizziness. To achieve this benefit, a water-resistant film or coating may be applied to the hair using film-forming polymers. Depending on the chemical make-up of the film-forming polymers. Product formulations that include these polymers can tend to be viscous, i.e. as the concentration of the polymer increases its viscosity builds up rapidly. Translated to styling applications, as the solvent evaporates, the polymer solution becomes thicker on the hair surface, leaving a sticky or tacky film residue on the hair. This often leaves hair with a stiff and/or "crunchy" feeling (i.e. the films become hard and brittle and therefore have a crunchy feel or sound when manipulated), which is undesirable to many consumers.

Increasingly, consumers also seek hair products that have a natural look and feel, impart good styling benefits to hair, are durable, and lack the drawbacks of current products, such as the stiff and crunchy effects created by the thick coatings of many styling products. Further, consumers seek products that offer multiple benefits, for example, combining frizz reduction and style hold with softening, straightening and curl definition. Moreover, consumers desire hair products that can protect hair from extreme environmental conditions such as high humidity which causes the hair to become very frizzy, unmanageable, and lose its shape and style.

One important functional element of such products is their ability to style the hair without weighing it down. Many consumers seek hair products which have excellent style memory, cosmeticity, and shine without heavily coating the hair strands, and thereby weighing the hair down and often times exhibiting a brittle or crunchy film. The resulting feel and texture of the hair after the application are important elements of such commodities. While different technologies and products exist in the market for hair styling products, there is still a need for improvement in these areas.

Thus, the object of this invention is related to a composition and method of styling hair utilizing hair compositions which will impart frizz control, and promote curl definition, softness, smoothness, shine and natural feel, but will not result in any product build up or leave the hair feeling heavily coated or weighed down, crunchy, stiff, or brittle. The object of the invention is also to provide these attributes that will last even when hair is exposed to high humidity conditions.

SUMMARY OF THE DISCLOSURE

It has surprisingly been found that compositions and methods of styling hair using a two phase or bi-phase system comprising a first phase which is an aqueous phase and a second phase which is an oily phase impart styling/shaping and other cosmetic benefits to the hair.

One aspect of the invention pertains to a hair treatment composition comprising:
(a) a first phase comprising:
  at least one non-polymeric mono, di, or tricarboxylic acid, and/or a salt thereof, and a mixture thereof;
  at least one amine selected from diamines, polyamines, alkylamines, alkanolamines, and a mixture thereof;
  at least one cationic polymer;
  at least one alkoxysilane;
  at least one polyol; and
  water; and
(b) a second phase comprising:
  at least one film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane; and
  at least one silicone oil.

In one embodiment, the first phase is aqueous and the second phase is an oil. In one or more embodiments, the at least one non-polymeric mono, di, or tricarboxylic acid, and/or a salt thereof, is a dicarboxylic acid and/or a salt thereof, and a mixture thereof. In some embodiments, the composition comprises at least one dicarboxylic acid and/or a salt thereof, and the at least one dicarboxylic acid and/or a salt thereof is selected from the group consisting of oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, and a salt thereof. In one or more embodiments, the at least one dicarboxylic acid and/or a salt thereof is maleic acid, malonic acid, and/or a salt thereof. In some embodiments, the composition comprises at least one tricarboxylic acid and/or a salt thereof, and the at least one tricarboxylic acid and/or a salt thereof is selected from the group consisting of citric acid, isocitric acid, aconitic acid, propane-1,2,3-tricarboxylic acid, benzene-1,3,5-tricarboxylic acid, and a thereof. In one or more embodiments, the at least one tricarboxylic acid and/or a salt thereof is citric acid, their salts thereof, and a mixture thereof. In some embodiments, the composition comprises at least 0.5 to about 20 wt. % of at least one non-polymeric mono, di, or tricarboxylic acid their salts thereof, and a mixture thereof, based on the total weight of the first phase of the hair treatment composition. In one or more embodiments, the composition comprises maleic acid.

In one or more embodiments, the composition the at least one amine includes one or more alkylamines and/or alkanolamines selected from the group consisting of compounds of formula (II):

$NR_3R_4R_5$      (II)

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some embodiments, the composition comprises one or more alkanolamines selected from the group consisting of monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and a mixture thereof. In one or more embodiments, the composition comprises monoethanolamine.

In one or more embodiments, the at least one polyol is selected from hexylene glycol, butylene glycol, propylene glycol, dipropylene glycol, caprylyl glycol, glycerin, and combinations thereof.

In one or more embodiments, the at least one polyol comprises hexylene glycol and butylene glycol.

Any of the above embodiments may be combined. For example, in some embodiments, the hair treatment composition comprises:

(a) a first phase comprising:
about 1 to about 5 wt. % of at least one non-polymeric mono, di, or tricarboxylic acid, and/or a salt thereof and a mixture thereof selected from oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, their salts thereof, and a mixture thereof;
about 0.5 to about 5 wt. % of at least one amine including one or more alkanolamines selected from monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and a mixture thereof;
about 0.2 to about 3 wt. % of at least one cationic polymer selected from poly(methacryloyloxyethyl trimethylammonium chloride), polyquaternium-37, quaternized cellulose derivatives, polyquaternium-4, polyquaternium-6, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof;
about 1.5 to about 8 wt. % of at least one alkoxysilane comprising 3-aminopropyltriethoxysilane;
about 1 to about 10 wt. % of at least one polyol comprising hexylene glycol and butylene glycol; and
at least 50 wt. % of water;
wherein all weights are based on the total weight of the first phase; and
(b) a second phase comprising:
about 0.06 to about 2% wt. % of at least one film-forming aminosilicone polymer selected from Polysilicone-29;
at least one silicone oil comprising cyclopentasiloxane;
optionally, at least one non-silicone oil; and
optionally, at least one organic solvent selected from polyols, C2 to C8 monoalcohols, and a mixture thereof;
wherein all weights are based on the total weight of the second phase.

Another aspect of the invention pertains to methods of treating hair. In some embodiments, the method comprises applying any of the compositions described herein to hair. In one or more embodiments, the composition is applied to hair as part of a shampoo or conditioning routine. In some embodiments, the composition is applied after a chemical relaxer is applied to the hair.

BRIEF DESCRIPTION OF THE DRAWING

Implementation of the present technology will now be described, by way of example only, with reference to the attached figures, wherein.

Figure 1A:
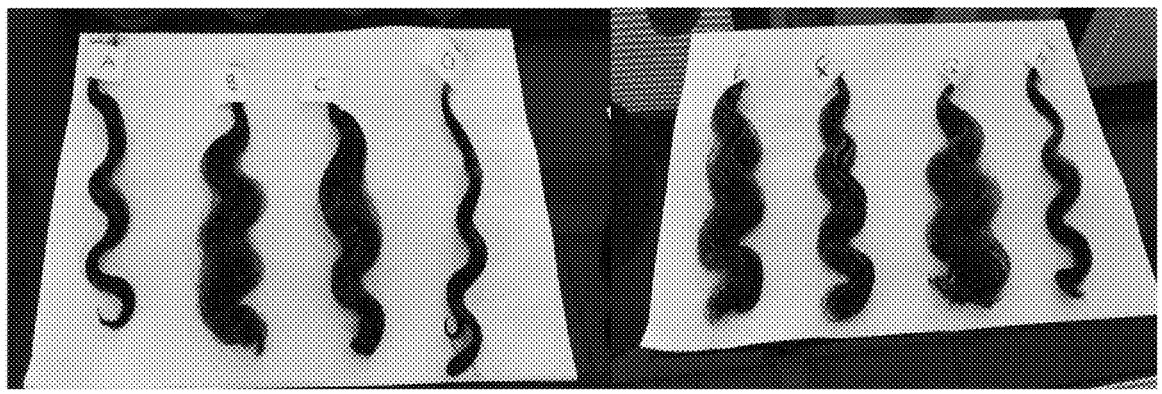
FIGS. 1a and 1b include pictures of hair swatches at the dry stage after treating the swatches with inventive or comparative bi-phase compositions.

It should be understood that the various aspects are not limited to the arrangements and instrumentality shown in the drawings.

DETAILED DESCRIPTION OF THE DISCLOSURE

The term "hair treatment composition" encompasses many types of compositions for application to the hair, for example, chemical relaxer compositions, shampoos, conditioners, hair-rinses, hair lotions, hair gels, mouse-type products, sprays, etc. A hair treatment composition is characterized by its ability to provide a cosmetic benefit to the hair. As is well-known, a shampoo provides cleansing benefits to the hair, a conditioner provides conditioning benefits to the hair, and gels can provide styling benefits to the hair. Non-limiting examples of additional benefits that can be imparted to hair include frizz control, curl definition, curl retention, smoothness, softness, suppleness, and natural feel.

The hair treatment compositions of the instant disclosure typically include:

(a) a first phase comprising:
  at least one non-polymeric mono, di, or tricarboxylic acid, and/or a salt thereof, and a mixture thereof;
  at least one amine selected from diamines, polyamines, alkylamines, alkanolamines, and a mixture thereof;
  at least one cationic polymer;
  at least one alkoxysilane;
  at least one polyol; and
  water; and (b) a second phase comprising:
  at least one film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane; and
  at least one silicone oil.

The above compositions, which feature a unique combinations of ingredients, advantageously provide frizz control, curl definition, curl retention, long lasting or humidity-resistant styling and curl care benefits together with natural feel, light-weight feel, softness, and smoothness.

The hair treatment compositions described herein may be in any suitable physical form. Suitable forms include, but are not limited to low to moderate viscosity liquids, lotions, milks, mousses, sprays, gels, creams, pastes, clays, bars, conditioners, and the like. For instance, spray formulations may be dispensed from containers that include aerosol dispensers or pump spray dispensers. Such dispensers are known in the art and are commercially available from a variety of manufacturers. When the spray formulation is dispensed from a pressurized aerosol container, a propellant may be used to force the composition out of the container. Suitable propellants include, but are not limited to, a liquefiable gas or a halogenated propellant. Examples of suitable propellants include dimethyl ether and hydrocarbon propellants such as propane, n-butane, iso-butane, CFCs, and CFC-replacement propellants. The propellants may be used singly or admixed. Furthermore, the hair treatment compositions may be in the form of an emulsion (e.g., water-in-oil or oil-in-water emulsion), wherein the first phase or the second phase or both include an emulsifier.

In an embodiment, the hair treatment composition of the present disclosure is substantially free of emulsifiers.

In an embodiment, the hair treatment composition of the present disclosure is bi-phasic. In an embodiment, the bi-phasic hair treatment composition is shaken up in a container or bottle before the composition is applied onto hair.

In some cases, the hair treatment composition of the present disclosure is in the form of a spray. In one embodiment, when the hair treatment is on the form of a spray, it does not contain a propellant (non-aerosol spray).

The hair treatment compositions may be packaged in a variety of different containers, such as, for example, a ready-to-use container. Non-limiting examples of useful packaging include tubes, jars, caps, unit dose packages, and bottles, including squeezable tubes and bottles and spray bottles.

The first phase and second phase according to the invention may be packaged in separate containers. In an embodiment, the separate containers may be part of a kit, and may be accompanied by instructions on mixing or combining before treating the hair with the mixture or layering the two phases onto hair.

Non-Polymeric Mono, Di, or Tricarboxylic Acid

A non-polymeric mono, di, and/or tricarboxylic acid is an organic compound having one (mono), two (di), or three (tri) carboxylic acid groups (—COOH). The non-polymeric mono, di, and tricarboxylic acids, and/or salts thereof, typically have a molecular weight of less than about 500 g/mol, less than about 400 g/mol, or less than about 300 g/mol.

Non-limiting examples of monocarboxylic acids, or salts thereof, include formic acid, acetic acid, propionic acid, butyric acid, valeric acid, caproic acid, entanthic acid, caprylic acid, pelargonic acid, capric acid, undecylic acid, lauric acid, tridecylic acid, lauric acid, tridecylic acid, myristic acid, pentadecylic acid, palmitic acid, margaric acid, stearic acid, nonadecylic acid, arachidic acid, lactic acid, a salt thereof, and a mixture thereof. In some cases, the hair treatment compositions include at least lactic acid and/or a salt thereof.

Non-limiting examples of dicarboxylic acids and/or salts thereof include oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, a salt thereof, and a mixture thereof. In some cases, the hair treatment compositions include oxalic acid, malonic acid, malic acid, maleic acid, a salt thereof, or a mixture thereof.

Non-limiting examples of tricarboxylic acids and salts thereof include citric acid, isocitric acid, aconitric acid, propane-1,2,3-tricarboxylic acid, benzene-1,3,5-tricarboxylic acid, a salt thereof, and a mixture thereof. In some instances, the hair treatment compositions include at least citric acid and/or a salt thereof.

In some cases, the hair treatment compositions include at least one or more dicaboxylic acids, and/or a salt thereof, in particular, oxalic acid, malonic acid, malic acid, maleic acid, a salt thereof, or a mixture thereof. A particularly useful dicarboxylic acid is malonic acid and/or a salt thereof. Another particularly useful dicarboxylic acid is maleic acid and/or a salt thereof.

The total amount of the at least one non-polymeric mono, di, or tricarboxylic acid, and/or a salt thereof, is at least 0.5 wt. %, based on the total weight of the first phase or the hair treatment composition. In some cases, the total amount of the at least one non-polymeric mono, di, or tricarboxylic acid, and/or salt thereof, is at least 0.5, 0.6, 0.7, 0.8, 0.9, or 1 wt. % up to about 15, 20 wt. %. Furthermore, the total amount of the at least one non-polymeric mono, di, or tricarboxylic acid, and/or salt thereof, may be at least 0.5 wt. % to about 20 wt. %, at least 0.5 wt. % to about 18 wt. %, at least 0.5 wt. % to about 15 wt. %, at least 0.5 wt. % to about 12 wt. %, at least 0.5 wt. % to about 10 wt. %, at least 0.5 wt. % to about 5 wt. %, at least 0.8 wt. % to about 20 wt. %, at least 0.8 wt. % to about 18 wt. %, at least 0.8 wt. % to about 15 wt. %, about 0.8 to about 12 wt. %, about 0.8 to about 10 wt. %, about 0.8 wt. % to about 5 wt. %, about 1 wt. % to about 20 wt. %, about 1 wt. % to about 18 wt. %, about 1 wt. % to about 15 wt. %, about 1 wt. % to about 12 wt. %, about 1 wt. % to about 10 wt. %, about 1 wt. % to about 8 wt. %, about 1 wt. % to about 6 wt. %, about 1 wt. % to about 5 wt. %, based on the total weight of the first phase or the hair treatment composition.

In some embodiments, the total amount of the at least one non-polymeric mono, di, or tricarboxylic acid, and/or salt thereof, may be at least 0.5 wt. % to about 20 wt. %, at least 0.6 wt. % to about 15 wt. %, at least 0.8 wt. % to about 12 wt. %, at least 0.8 wt. % to about 10 wt. %, at least 1 wt. % to about 8 wt. %, at least 1 wt. % to about 6 wt. %, or at least 1 wt. % to about 5 wt. %, based on the total weight of the first phase or the hair treatment composition.

Amines

Non-limiting examples of the types of amines that may be used in the hair treatment compositions are vast, but may include diamines, polyamines, alkylamines, alkanolamines, and mixtures thereof. The one or more amines may be primary, secondary, tertiary amines, and mixtures thereof.

Diamines

Non-limiting examples of diamines that may be useful may be primary amines and secondary amines. The diamine can include both primary and secondary amine groups. Optional diamines may include at least one ethylene oxide group. For example, between 1 and 4 ethylene oxide groups can be present in the diamine. The diamine may optionally include propylene oxide groups. For example, between 1 and 4 propylene oxide groups can be present in the diamine. Non-limiting examples of diamines include 4,9-dioxadodecane-diamine; 4, 7, 10-trioxa-1,13-tridecanediamine; ethylenediamino; polyoxypropylene diamine; polyethylene glycol diamine; triethylene glycol diamine (20E); n-(2-hydroxyethyl)-ethylenediamine; 1,3-diaminopropane; 1,7-diaminoheptane; 1,4-diaminobutane; 1,2-diaminopropane; 1,6-diaminohexane; 1,11-diamino-3,6,9-trioxaundecane; 1,5-diaminopentane; polyoxyethylene diamine; 2,2-dimethyl-1,3-propanediamine; 2,2-bis(aminoethoxy)propane; 4,7,10-trioxa-1,13-tridecanediamine; 1,3-diaminopentane; 4,7,10-trioxa-1,13; 1,5-diamino-2-methylpentane; (3s,4s)-(−)-3,4-hexanediamine dihydrochloride; 1,9-diaminononane, and mixtures thereof.

In some cases, diamines may be selected from the group consisting of 4,9-dioxadodecane-diamine, 4, 7, 10-trioxa-1,13-tridecanediamine, ethylenediamino, polyoxypropylene diamine, polyethylene glycol diamine, triethylene glycol diamine (20E); n-(2-hydroxyethyl)-ethylenediamine; 1,3-diaminopropane, 1,7-diaminoheptane, 1,4-diaminobutane, 1,2-diaminopropane, 1,6-diaminohexane, 1,11-diamino-3,6,9-trioxaundecane, 1,5-diaminopentane, polyoxyethylene diamine, 2,2-dimethyl-1,3-propanediamine, 2,2-bis(aminoethoxy)propane, 4,7,10-trioxa-1,13-tridecanediamine, 1,3-diaminopentane, 4,7,10-trioxa-1,13; 1,5-diamino-2-methylpentane, (3s,4s)-(−)-3,4-hexanediamine dihydrochloride, 1,9-diaminononane, and mixtures thereof.

Polyamines

Polyamines have more than two amino groups. In some cases, the composition of the instant disclosure may include one or more polyamines, but in some cases, the compositions are free or essentially free of polyamines. The polyamine may be, for example, aminated polysaccharides comprising multiple amino groups, such as, for example, hydrolysates of aminated polysaccharides.

The polyamine may also be a polymer comprising multiple amino groups including homopolymers, copolymers, and terpolymers.

In some cases, polyamines are chosen from polyethyleneimines. Polyethyleneimines may optionally be substituted. Non-limiting examples of polyethyleneimines which may be used include LUPASOL products commercially available from BASF. Suitable examples of LUPASOL polyethyleneimines include LUPASOL PS, LUPASOL PL, LUPASOL PR8515, LUPASOL G20, LUPASOL G35 as well as LUPASOL SC Polythyleneimine Reaction Products (such as LUPASOL SC-61B, LUPASOL SC-62J, and LUPASOL SC-86X). Other non-limiting examples of polyethyleneimines which may be used in the composition according to the present invention are the EPOMIN products commercially available from Aceto. Suitable examples of EPOMIN polyethyleneimines include EPOMIN SP-006, EPOMIN SP-012, EPOMIN SP-018, and EPOMIN P-1000. Suitable polyamines s also be chosen from polyvinylamines. Examples thereof include LUPAMINES 9095, 9030, 9010, 5095, 1595 from BASF.

The polyamine compounds can also be substituted. An example of such a compound is PEG-15 Cocopolyamine from Cognis.

In some cases, the polyamine is chosen from proteins and protein derivatives. Non-limiting examples of suitable proteins and protein derivatives f include those listed at pages 1701 to 1703 of the C.T.F.A. International Cosmetic Ingredient Dictionary and Handbook, 8$^{th}$ edition, vol. 2, (2000), which is incorporated herein by reference in its entirety. In some cases, the at least one polyamine is chosen from wheat protein, soy protein, oat protein, collagen, and keratin protein.

The polyamine may be an alkoxylated polyamine. The alkoxylated polyamines may be chosen from amine compounds having at least two amino groups and at least one degree of alkoxylation. The alkoxylation is provided by an alkylene oxide group which may be chosen from ethylene oxide and propylene oxide. Non-limiting examples of suitable alkoxylated polyamines include compounds corresponding to the following formula:

wherein R represents a —CH2-, —CH$_2$CH$_2$—, —CHCH$_3$— or —C(CH$_3$)$_2$— group, or a hydrocarbon radical containing at least 3 carbon atoms that is linear or branched, acyclic or cyclic, saturated or unsaturated, aliphatic or aromatic, substituted or unsubstituted; x, y, and z independently of one another, represent numbers of from 0 to about 100; R' represents hydrogen, or an alkyl group, preferably a methyl group; and The sum of x+y+z is at least 1. In some cases, R is a linear or branched, acyclic alkyl or alkenyl group or an alkyl phenyl group; x, y, and z independently of one another, preferably represent numbers ranging from 2 to 100.

Non-limiting examples of the alkoxylated polyamines include, for example, tetradecyloxypropyl-1,3-diaminopropane; a C$_{12-14}$ alkyl oxypropyl-1,3-diaminopropane; a C$_{12-15}$ alkyloxypropyl amine and other similar materials that are commercially available from Tomah under the tradename of TOMAH DA-17. Other examples of alkoxylated polyamines are diamine compounds belonging to the Jeffamine series such as the JEFFAMINE D and JEFFAMINE ED series available from Huntsman Corporation, Salt Lake City, Utah. Examples of these Jeffamine compounds are JEFFAMINE D230, JEFFAMINE D400, JEFFAMINE D2000, JEFFAMINE D4000, JEFFAMINE HK-511, JEFFAMINE ED600, JEFFAMINE ED900, and JEFFAMINE ED2003. JEFFAMINE D series compounds are amine terminated PPGs (polypropylene glycols) and JEFFAMINE ED series compounds are polyether diamine based with a predominantly PEG (polyethylene glycol) backbone.

Other non-limiting examples of suitable alkoxylated polyamines in the diamine form include compounds corresponding to the following formula:

$$NH_2(CH_2)_xOCH_2CH_2O(CH_2)_xNH_2$$

wherein x is 2 or 3.

Examples of alkoxylated polyamines are diamine compounds belonging to the JEFFAMINE series available from Huntsman Corporation, Salt Lake City, Utah, such as JEFFAMINE EDR148, and JEFFAMINE EDR176.

Additional non-limiting examples of alkoxylated polyamines in the triamine form include compounds corresponding to the following formula:

$$NH_2(CHCH_3CH_2O)_xCH_2C(R)CH_2(OCH_2CHCH_3)_zNH_2$$
$$|$$
$$(CH_2)_n(OCH_2CHCH_3)_yNH_2$$

wherein R is hydrogen, —$CH_2$ or —$C_2H_5$, n=0 or 1, and x, y, and z independently of one another, represent numbers of from 0 to 100 and the sum of x+y+z is at least 1.

Examples of alkoxylated polyamines are triamine compounds belonging to the JEFFAMINE series such as the JEFFAMINE T series available from Huntsman Corporation, Salt Lake City, Utah. Examples of the JEFFAMINE T series compounds are JEFFAMINE T403, JEFFAMINE T3000, and JEFFAMINE T5000. JEFFAMINE T series compounds are triamines made by reacting PO with a triol initiator followed by aminating the terminal hydroxyl groups.

Alkylamines and Alkanolamines

The one or more alkylamines and/or one or more alkanolamines that may be included in the compositions include compounds of formula (II):

$$NR_3R_4R_5 \qquad (II)$$

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl. In some cases, $R_3$, $R_4$ and $R_5$ are independently H, $C_1$-$C_2$ alkyl, $C_1$-$C_{20}$ monohydroxyalkyl or $C_2$-$C_{20}$ polyhydroxyalkyl, provided that at least one of $R_3$, $R_4$ and $R_5$ is an alkyl or mono or polyhydroxyalkyl. Finally, $R_3$, $R_4$ and $R_5$ may independently be H, $C_1$-$C_{10}$ alkyl, $C_1$-$C_{10}$ monohydroxyalkyl or $C_2$-$C_{10}$ polyhydroxyalkyl, provided that at least one of $R_3$, $R_4$ and $R_5$ is an alkyl or mono or polyhydroxyalkyl.

Non-limiting examples of alkanolamines include monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and mixtures thereof. In some cases, the compositions include at least monoethanol amine. In some cases, the compositions include at least monoethanolamine.

Further non-limiting examples of alkylamines include aliphatic amine compounds corresponding to the following formula and their salts:

$$RN(R')_2$$

wherein R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and the groups R', which may be identical or different, represent H or a hydrocarbon radical containing less than 6 carbon atoms. In addition, the groups R', which may be identical or different, are linear or branched, acyclic or cyclic, saturated or unsaturated, substituted or unsubstituted. In some cases, the groups R', which may be identical or different, are H or a methyl group.

In some cases, alkylamines include, but are not limited to the following examples: dimethyl lauramine, dimethyl behenamine, dimethyl cocamine, dimethyl myristamine, dimethyl palmitamine, dimethyl stearamine, dimethyl tallowamine, dimethyl soyamine, stearamine, soyamine, cocamine, lauramine, palmitamine, oleamine, tallow amine and mixtures thereof.

Other non-limiting examples of alkyl monoamines include amidoamine compounds corresponding to the following formula and their salts:

$$RCONHR'N(R'')_2$$

wherein: R is a hydrocarbon radical containing at least 6 carbon atoms. In addition, R can be linear or branched, acyclic or cyclic, saturated or unsaturated, aliphatic or aromatic, substituted or unsubstituted. Typically, R is a linear or branched, acyclic alkyl or alkenyl group or an alkyl phenyl group; and R' is a divalent hydrocarbon radical containing less than 6 carbon atoms, or 2 or 3 carbon atoms, and R" is H or a hydrocarbon radical containing less than 6 carbon atoms. In addition, R" is linear or branched, acyclic or cyclic, saturated or unsaturated, substituted or unsubstituted. Typically, R" is a linear or branched, acyclic alkyl or alkenyl group. In some cases, R" is H or a methyl group.

Examples of amidoamines that are useful in the compositions of the instant disclosure include, but are not limited to the following: oleamidopropyl dimethylamine, stearamidopropyl dimethylamine, isostearamidopropyl dimethylamine, stearamidoethyl dimethylamine, lauramidopropyl dimethylamine, myristamidopropyl dimethylamine, behenamidopropyl dimethylamine, dilinoleamidopropyl dimethylamine, palmitamidopropyl dimethylamine, ricinoleamindopropyl dimethylamine, soyamidopropyl dimethylamine, wheat germamidopropyl dimethylamine, sunflowerseedamidopropyl dimethylamine, almondamidopropyl dimethylamine, avocadoamidopropyl dimethylamine, babassuamidopropyl dimethylamine, cocamidopropyl dimethylamine, minkamidopropyl dimethylamine, oatamidopropyl dimethylamine, sesamidopropyl dimethylamine, tallamidopropyl dimethylamine, brassicaamidopropyl dimethylamine, olivamidopropyl dimethylamine, palmitamidopropyl dimethylamine, stearamidoethyldiethylamine, and mixtures thereof.

Additional Amines

Additional amines that may be useful include alkoxylated monoamines. The alkoxylated monoamines are compounds having an amino group and at least one degree of alkoxylation. The alkoxylation is provided by an alkylene oxide group which is often chosen from ethylene oxide and propylene oxide.

Non-limiting examples of suitable alkoxylated monoamines include compounds corresponding to the following formula:

$$RN[(R'CHCH_2O)_xH][(R'CHCH_2O)_yH]$$

wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 provided that the sum of x+y is >0; the groups R', which may be identical or different, represent hydrogen, or an alkyl group such as a methyl group. Typically, R is a linear or branched, acyclic alkyl or alkenyl group or an alkyl phenyl group; x and y, independently of one another, are each typically a number from 0 to 30. Typically, one R' group is hydrogen, and the other one is methyl.

Non-limiting examples of alkoxylated monoamines include PEG-2 Cocamine, PEG-3 Cocamine, PEG-5 Cocamine, PEG-10 Cocamine, PEG-15 Cocamine, PEG-20 Cocamine, PEG-2 Lauramine, PEG-12 Palmitamine, PEG-2 Rapeseedamine, PEG-2 Oleamine, PEG-5 Oleamine, PEG-6 Oleamine, PEG-10 Oleamine, PEG-15 Oleamine, PEG-20 Oleamine, PEG-25 Oleamine, and PEG-30 Oleamine. Other examples are alkoxylated derivatives of soyamine, stearamine and tallow amine.

Other non-limiting examples of suitable alkoxylated monoamines include compounds corresponding the following formula:

RNR"[(R'CHCH$_2$O)$_x$H]

wherein R is a hydrocarbon radical containing at least 6 carbon atoms. R can be linear or branched, acyclic or cyclic, saturated or unsaturated, aliphatic or aromatic, substituted or unsubstituted; x represents a number of from 1 to 100; R' represents hydrogen, or an alkyl group such as in particular a methyl group; and R" is a hydrogen or a hydrocarbon radical. Typically, R is a linear or branched, acyclic alkyl or alkenyl group or an alkyl phenyl group; x is typically a number from 1 to 30. When R" is a hydrocarbon radical group, this group may be linear or branched, saturated or unsaturated, substituted or unsubstituted. The hydrocarbon radical represented by R" may also contain an alkoxylated moiety (as defined by [(R'CHCH$_2$O)$_y$H]), and/or heteroatoms such as nitrogen. When R" contains at least one alkoxylated moiety, the total number of alkoxylation in the formula may range from 1 to 120. Examples of alkoxylated monoamines include PEG-3 Tallow Aminopropylamine, PEG-10 Tallow Aminopropylamine, PEG-15 Tallow Aminopropylamine, and PEG-105 Behenyl Propylenediamine.

Additional non-limiting examples of alkoxylated monoamines include compounds corresponding to the following formula:

R(R'CHCH$_2$O)$_x$(R'CHCH$_2$O)$_y$NH$_y$, wherein R is a hydrocarbon radical containing at least 6 carbon atoms. R can be linear or branched, acyclic or cyclic, saturated or unsaturated, aliphatic or aromatic, substituted or unsubstituted; x and y, independently of one another, represent numbers of from 0 to 100 with the proviso that the sum of x+y is >0; the groups R', which may be identical or different, represent hydrogen, or an alkyl group such as in particular a methyl group. Typically, R is a linear or branched, acyclic alkyl or alkenyl group or an alkyl phenyl group; x and y, independently of one another, are each typically a number from 0 to 30. Examples of alkoxylated monoamines include polyetheramines containing a monoamine group. These polyetheramines are commercially available from Hunstman under the tradename JEFFAMINE (M series such as M-600, M-1000, M-2005 and M-2070) and SURFONAMINE series (B-60, B-100, B-200, L-100, L-200, L-207, L-300).

The total amount of the at least one amine may vary, but in some cases, the total amount is about 0.1 to about 20 wt. %, based on the total weight of the first phase or the hair treatment composition. In some cases, the total amount of the at least one amine is about 0.1 to about 20 wt. %, about 0.1 to about 18 wt. %, about 0.1 to about 15 wt. %, about 0.1 to about 12 wt. %, about 0.1 to about 10 wt. %, about 0.1 to about 8 wt. %, about 0.1 to about 5 wt. %, about 0.5 to about 20 wt. %, about 0.5 to about 18 wt. %, about 0.5 to about 15 wt. %, about 0.5 to about 12 wt. %, about 0.5 to about 10 wt. %, about 0.5 to about 8 wt. %, about 0.5 to about 5 wt. %, about 0.8 to about 20 wt. %, about 0.8 to about 18 wt. %, about 0.8 to about 15 wt. %, about 0.8 to about 12 wt. %, about 0.8 to about 10 wt. %, about 0.8 to about 8 wt. %, or about 0.8 to about 5 wt. %.

In some embodiments, the total amount of the at least one amine may be at least 0.1 wt. % to about 20 wt. %, at least 0.2 wt. % to about 15 wt. %, at least 0.4 wt. % to about 10 wt. %, at least 0.5 wt. % to about 10 wt. %, at least 0.5 wt. % to about 8 wt. %, at least 0.5 wt. % to about 6 wt. %, or at least 0.5 wt. % to about 5 wt. %, based on the total weight of the first phase or the hair treatment composition.

Cationic Polymer

Non-limiting examples of cationic polymers include poly (methacryloyloxyethyl trimethylammonium chloride), polyquaternium-37, quaternized cellulose derivatives, polyquaternium-4, polyquaternium-10, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, and a mixture thereof. In some instances, the one or more cationic polymers may be selected from the group consisting of polyquaternium-4, polyquaternium-10, cationic guar derivatives, and a mixture thereof.

The cationic polymers can be a monoalkyl quaternary amine, such as stearyltrimonium chloride, soyatrimonium chloride or coco-ethyldimonium ethosulfate. Other suitable cationic polymers include, but are not limited to, behentrimonium chloride, dialkyl quaternary amines, such as dicetyldimonium chloride, dicocodimethyl ammonium chloride or distearyldimethyl ammonium chloride; and polyquaternium compounds, such as Polyquaternium-6, Polyquaternium-22 or Polyquaternium-5.

For example, cationic polymers may be chosen from polyquaterium-10 (also called quaternized polyhydroxyethyl cellulose), cetrimonium chloride (also called cetyl trimethyl ammonium chloride, CTAC), behentrimonium chloride (also known as docosyl trimethyl ammonium chloride), behentrimonium methosulfate, steartrimonium chloride, stearalkonium chloride, dicetyldimonium chloride, hydroxypropyltrimonium chloride, cocotrimonium methosulfate, olealkonium chloride, steartrimonium chloride, babassuamidopropalkonium chloride, brassicamidopropyl dimethylamine, Quaternium-91, Salcare/PQ-37, Quaternium-22, Quaternium-87, Polyquaternium-4, Polyquaternium-6, Polyquaternium-11, Polyquaternium-44, Polyquaternium-67, amodimethicone, lauryl betaine, Polyacrylate-1 Crosspolymer, steardimonium hydroxypropyl hydrolyzed wheat protein, behenamidopropyl PG-dimonium chloride, lauryldimonium hydroxypropyl hydrolyzed soy protein, aminopropyl dimethicone, Quaterium-8, and dilinoleamidopropyl dimethylamine dimethicone PEG-7 phosphate.

In some instances, the cationic polymers are cationic conditioning polymers. Examples of cationic conditioning polymers that can be used include, without limitation, cationic cellulose, cationic proteins, and cationic polymers. The cationic polymers can have a vinyl group backbone of amino and/or quaternary ammonium monomers. Cationic amino and quaternary ammonium monomers include, without limitation, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salts, diallyl quaternary ammonium salts, vinyl compounds substituted with dialkyl aminoalkyl acrylate, and vinyl quaternary ammonium monomers having cyclic cationic nitrogen containing rings such as pyridinium, imidazolium, or quaternized pyrrolidine. Other examples of cationic conditioning polymers that can be used include, without limitation, hydroxypropyltrimonium honey, cocodimonium silk amino acids, cocodimonium hydroxypropyl hydrolyzed wheat or silk protein, polyquaternium-5, polyquaternium-11, polyquaternium-2, polyquaternium-4, polyquaternium-6, polyquaternium-7, polyquaternium-14, polyquaternium-16, polyquaternium-22, polyquaternium-10, and guar hydroxypropyltrimonium chloride.

In some cases quaternized polymeric cationic polymers are particularly useful. Particularly preferred are quaternary nitrogen polymers prepared by the polymerization of a dialkyldiallylammonium salt or copolymer thereof in which the alkyl group contains 1 to about 18 carbon atoms, and more preferably where the alkyl group is methyl or ethyl. Details concerning the preparation of these polymers can be found in U.S. Pat. Nos. 3,288,770, 3,412,019 and 4,772,462, incorporated herein by reference. For example, cationic homopolymers and copolymers of polydiallyldimethylammonium chloride are available in aqueous compositions sold under the trademark MERQUAT by the Calgon Corporation, subsidiary of Merck & Co., Pittsburgh, Pa. The homopolymer, which is named Polyquaternium-6 is sold under the trademark MERQUAT-100, and is described as having a weight average molecular weight of approximately 100,000. A copolymer reaction product of dimethyldiallylammonium chloride with acrylamide monomers is named Polyquaternium-7 is described as having a weight average molecular weight of approximately 500,000 and is sold under the trademark MERQUAT-550. Another copolymer reaction product of dimethyldiallylammonium chloride with acrylic acids having a weight average molecular weight from about 50,000 to about 10,000,000 has the name Polyquaternium-22 and is sold under the trademark MERQUAT-280. Polyquaternium-6 is particularly preferred.

Other polymeric conditioners include cationic copolymers of methylvinylimidazolium chloride and vinyl pyrrolidone, sold commercially by BASF Aktiengesellschaft, West Germany under the trademark LUVIQUAT at three comonomer ratios, namely at ratios of 95/5, 50/50 and 30/70 methylvinylimidazolium chloride to polyvinylpyrrolidone. These copolymers at all three comonomer ratios have the name Polyquaternium 16. Polymeric conditioners also include cationic cellulosic polymers of hydroxyethyl cellulose reacted with epichlorohydrin and quaternized with trimethylamine, sold under the trademark POLYMER JR in various viscosity grades and molecular sizes by Union Carbide Corporation, Danbury, Conn. These series of polymers are named Polyquaternium 10. Also useful are quaternized copolymers of hydroxyethylcellulose and dimethyldimethylammonium chloride, having the name Polyquaternium-4, sold in varying molecular weights under the trademark CELQUAT by National Starch and Chemical Corporation, Bridgewater, N.J.

Smaller molecule cationic non-polymeric conditioning agents can also be utilized herein. Exemplary small-molecule conditioning agents can include monofunctional or difunctional quaternary ammonium compounds, such as stearyldimethylbenzylammonium chloride, dimethyldi-(hydrogenated tallow)ammonium chloride, and the like. Non-polymeric conditioning agents can also include the quaternary ammonium salts of gluconamide derivatives, such as gamma-gluconamidopropyldimethyl-2-hydroxyethyl-ammonium chloride and minkamidopropyldimethyl-2-hydroxyethylammonium chloride identified respectively by the names Quaternium 22 and Quaternium 26. Details for the preparation of these materials are found in U.S. Pat. Nos. 3,766,267 and 4,012,398, respectively, and the materials are sold under the trademark CERAPHYL by Van Dyk & Co., Belleville, N.J. Also useful are bis-quaternary ammonium compounds which are dimers, such as 2-hydroxy propylene-bis-1,3-(dimethylstearyl ammonium chloride, designated the name, Hydroxypropyl Bisstearyldimonium chloride. The preparation of these and other bis-quat materials is described in U.S. Pat. No. 4,734,277, and such materials are sold under the trademark JORDAQUAT DIMER by Jordan Chemical Company, Folcroft, Pa.

Exemplary unquaternized polymers having tertiary amino nitrogen groups that become quaternized when protonated can include water-soluble proteinaceous quaternary ammonium compounds. hydrolyzed animal protein, for example, is the name for a chemically-modified quaternary ammonium derivative of hydrolyzed collagen protein having from about 12 to about 18 carbons in at least one aliphatic alkyl group, a weight average molecular weight from about 2500 to about 12,000, and an isoionic point in a range from about 9.5 to about 11.5. This material and structurally related materials are sold under the trademarks CROQUAT and CROTEIN by Croda, Inc., New York, N.Y.

Alkoxysilane

The at least one alkoxysilane often includes at least one solubilizing functional group. As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents. Suitable solubilizing functional groups include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

In some cases, the at least one alkoxysilane comprising at least one solubilizing functional group may comprise two or three alkoxy groups. For example, the alkoxy functional groups may be chosen from methoxy and ethoxy functional groups.

In some cases, the at least one alkoxysilane comprising at least one solubilizing functional group may be selected from compounds of the following formula:

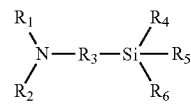

wherein, $R_4$ is chosen from halogen atoms, OR' groups, and $R_{11}$ groups;

$R_5$ is chosen from halogen atoms, OR" groups, and $R_{12}$ groups;

$R_6$ is chosen from halogen atoms, OR''' groups, and $R_{13}$ groups;

$R_1$, $R_2$, $R_3$, R', R", R''', $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R", and R''' may also be chosen from hydrogen; provided that at least two groups $R_4$, $R_5$, and $R_6$ are different from $R_{11}$, $R_{12}$, and $R_{13}$, and at least two groups R', R", and R''' are not hydrogen.

The at least one alkoxysilane comprising at least one solubilizing functional group may also be one or more compounds chosen from compounds of the following formula:

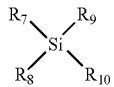

wherein $R_9$ is chosen from halogen atoms and $OR'_9$ groups;

$R_{10}$ is chosen from halogen atoms and $OR'_1$ groups;

$R'_9$ and $R'_{10}$, which may be identical or different, are chosen from hydrogen, and linear and branched, saturated and unsaturated $C_1$-$C_{14}$ hydrocarbon groups $R_7$ is a non hydrolyzable functional group providing a cosmetic effect; and $R_8$ is a non hydrolyzable functional group bearing at least one function chosen from amines, carboxylic acids and salts thereof, sulfonic acids and salts thereof, polyols such as glycol, polyethers such as polyalkylene ether, and phosphoric acids and salts thereof; and provided that at least one of $R_9$ and $R_{10}$ is not a halogen.

In some cases, the at least one alkoxysilane comprising at least one solubilizing functional group may be chosen from compounds of the following formula:

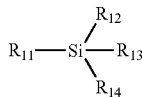

wherein $R_{12}$ is chosen from halogen atoms, $OR'_{12}$ groups, and $R_O$ groups;

$R_{13}$ is chosen from halogen atoms, $OR'_{13}$ groups, and $R'_O$ groups;

$R_{14}$ is chosen from halogen atoms, $OR'_{14}$ groups, and $R''_O$ groups;

$R_{11}$ is chosen from groups bearing at least one function chosen from carboxylic acids and salts thereof, sulfonic acids and salts thereof, and polyalkyethers;

Ro, R'o, R"o, $R'_{12}$, $R'_{13}$, and $R'_{14}$, which may be identical or different, are chosen from linear and branched, saturated and unsaturated, C1-$C_{14}$ hydrocarbon groups optionally bearing at least one additional chemical functional group chosen from carboxylic acids and salts thereof, sulfonic acids and salts thereof, and polyalkyether functions, and wherein $R'_{12}$, $R'_{13}$, and $R_{14}$ may also be chosen from hydrogen; provided that at least two groups from $R_{12}$, $R_{13}$ and $R_{14}$ are different from $R_O$, $R'_O$, and $R''_O$ groups; and provided further that at least two of the groups $R'_{12}$, $R'_{13}$, and $R'_{14}$ are not hydrogen.

According to another embodiment, the at least one alkoxysilane comprising at least one solubilizing functional group may be chosen from compounds of the following formula:

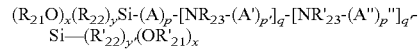

wherein $R_{21}$, $R_{22}$, $R'_{21}$, and $R'_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x is an integer ranging from 1 to 3;

y is 3-x;

x' is an integer ranging from 1 to 3;

y' is 3-x', p, p', p", q, and q' can each be 0 or 1, wherein at least one of q or q' is not equal to zero;

A, A', and A", which may be identical or different, are chosen from linear and branched $C_1$-$C_{20}$ alkylene divalent radicals; and $R_{23}$ and $R'_{23}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

The at least one alkoxysilane comprising at least one solubilizing functional group may also be chosen from compounds of the following formula:

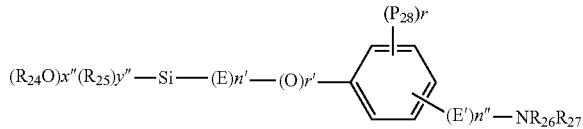

wherein $R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

x" is 2 or 3; [0170] y" is 3-x";

n' is 0 or 1;

n" is 0 or 1;

E and E', which may be identical or different, are chosen from linear and branched $C_1$-$C_{20}$ alkylene divalent radicals;

$R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_1$-$C_{20}$ alcohol ester, amine, amide, carboxyl, alkoxysilane, hydroxyl, carbonyl, and acyl groups;

r is an integer ranging from 0 to 4;
r'=0 or 1; and
$R_{28}$ is chosen from hydrogen and linear and branched, saturated and unsaturated hydrocarbon chains, comprising, optionally at least one heteroatom, optionally interrupted by or substituted with at least one entity chosen from ether, alkyl alcohol ester, amine, carboxyl, alkoxysilane, alkyl aryl, hydroxyl, and carbonyl groups, and aromatic, heterocyclic, and non-heterocyclic rings.

According to a further exemplary embodiment, the at least one alkoxysilane comprising at least one solubilizing functional group may be chosen from compounds of the following formula:

$(R_{29}O)x_1(R_{30})y_1\text{-Si-}(A_1)_s\text{-CH=O}$ wherein $R_{29}$ and $R_{30}$, independently, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups;

$x_1$ is 2 or 3;
$y_1$ is $3\text{-}x_1$;
$A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_6$-$C_{30}$ aryl, hydroxyl, and carbonyl groups; and s is 0 or 1.

In some instances, the at least one alkoxysilane comprising at least one solubilizing functional group is chosen from compounds of the following formula:

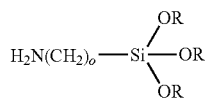

wherein the R radicals, which may be identical or different, are chosen from $C_1$-$C_6$ alkyl radicals and n is an integer ranging from 1 to 6, for example, from 2 to 4.

The alkoxysilanes useful in the present disclosure can be chosen from alkoxysilanes comprising a silicon atom in a formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Exemplary alkoxysilanes include, but are not limited to, 3-mercaptopropyltriethoxysilane and aminoalkyltrialkoxysilanes such as 3-aminopropyltriethoxysilane, as described in French Patent Application No. FR2789896, incorporated by reference herein. Other useful alkoxysilanes are cited, for example, in EP1216022, incorporated by reference herein, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST. In some cases, the alkoxysilanes may comprise at least one hydrocarbon chain containing fluorine atoms. Non-limiting examples include but are not limited to the 3,3,3-trifluoropropyltriethoxysilane or tridecafluorooctyltriethoxysilane compounds described in EP1510197, incorporated by reference herein.

It is also contemplated that these alkoxysilanes may carry a solubilizing, non-hydrolysable group such as amino groups, carboxylic acids, sulphonic acids, sulphates, quaternary ammoniums, polyalcohols, polyether and phosphates. One possible example of the foregoing types of alkoxysilanes is aminopropyl-N-(4,2-dinitrophenyl)aminopropyldiethoxysilane. Additional exemplary compounds of this type are described, for example, in EP1216023, which is herein incorporated by reference. Non-limiting examples of useful alkoxysilanes include 3-mercaptopropyltriethoxysilane and aminoalkyltrialkoxysilanes such as 3-aminopropyltriethoxysilane ("APTES", described in French Patent Application No. FR 2 789 896, incorporated herein by reference), and mixtures thereof. In some cases, the hair-treatment compositions include 3-aminopropyltriethoxysilane.

The total amount of the at least one alkoxysilane may vary, but in some cases, the total amount is about 0.1 to about 20 wt. %, based on the total weight of the first phase or the hair treatment composition. In some cases, the total amount of the at least one alkoxysilane is about 0.1 to about 20 wt. %, about 0.1 to about 18 wt. %, about 0.1 to about 15 wt. %, about 0.1 to about 12 wt. %, about 0.1 to about 10 wt. %, about 0.1 to about 8 wt. %, about 0.1 to about 5 wt. %, about 0.5 to about 20 wt. %, about 0.5 to about 18 wt. %, about 0.5 to about 15 wt. %, about 0.5 to about 12 wt. %, about 0.5 to about 10 wt. %, about 0.5 to about 8 wt. %, about 0.5 to about 5 wt. %, about 0.8 to about 20 wt. %, about 0.8 to about 18 wt. %, about 0.8 to about 15 wt. %, about 0.8 to about 12 wt. %, about 0.8 to about 10 wt. %, about 0.8 to about 8 wt. %, about 0.8 to about 5 wt. %, about 1 to about 20 wt. %, about 1 to about 18 wt. %, about 1 to about 15 wt. %, about 1 to about 12 wt. %, about 1 to about 10 wt. %, about 1 to about 8 wt. %, about 1 to about 5 wt. %, about 1.5 to about 20 wt. %, about 1.5 to about 18 wt. %, about 1.5 to about 15 wt. %, about 1.5 to about 12 wt. %, about 1.5 to about 10 wt. %, about 1.5 to about 8 wt. %, or about 1.5 to about 5 wt. %.

In some embodiments, the total amount of the at least one alkoxysilane may be at least 0.1 wt. % to about 20 wt. %, at least 0.5 wt. % to about 15 wt. %, at least 1 wt. % to about 10 wt. %, at least 1.5 wt. % to about 10 wt. %, at least 1.5 wt. % to about 8 wt. %, at least 1.5 wt. % to about 5 wt. %, or at least 1.5 wt. % to about 3 wt. %, based on the total weight of the first phase or the hair treatment composition.

Polyols

In one or more embodiments, the at least one polyol comprises one or more glycol compounds. In further embodiments, the glycol compounds are selected from the group consisting of hexylene glycol, butylene glycol, propylene glycol, dipropylene glycol, and combinations thereof. In other embodiments, the at least one polyol comprises glycerin.

In one or more embodiments, the at least one polyol comprises a mixture of two ingredients in a ratio ranging from about 1:2 to about 2:1, or more specifically about 1:1. In some embodiments, the at least one comprises hexylene glycol and butylene glycol. In one or more embodiments, the at least one polyol comprises propylene glycol in addition to hexylene glycol and butylene glycol.

While not wishing to be bound to any particular theory, it is thought that the presence of the polyol increases the efficacy of penetrating actives such as maleic acid. The polyol may also act as a surfactant and assists in stabilizing the emulsion. Emulsion stability is a particularly important effect when low pH ingredients are present (e.g., maleic acid) because such low pH ingredients can have a negative effect on emulsion stability. Thus, it is thought that the at least one polyol works to counteract the negative effect of low pH ingredients on emulsion stability as well as assisting active penetration to the cortex.

In some embodiments, the total amount of the at least one polyol may be at least 0.1 wt. % to about 20 wt. %, at least 0.5 wt. % to about 15 wt. %, at least 1 wt. % to about 12 wt. %, at least 1.5 wt. % to about 10 wt. %, at least 1.5 wt. % to about 8 wt. %, at least 1.5 wt. % to about 5 wt. %, based on the total weight of the first phase or the hair treatment composition.

Water

The amount of water in the first phase or hair treatment compositions may be at least 50 wt. %, or from about 50 to about 95 wt. %, about 50 to about 90 wt. %, about 50 to about 85 wt. %, about 60 to about 80 wt. %.

Film-Forming Aminosilicone Polymer

In accordance with some embodiments, the at least one film-forming aminosilicone polymer comprises Polysilicone-29, which is a film-forming aminosilicone polymer formed by the reaction between a glycidoxypropyl-terminated dimethyl siloxane polymer, PEG-13 diglycidyl ether, diethylaminopropylamine, and aminopropyltriisopropoxysilane sold under the tradename SILSOFT CLX-E emulsion (Momentive Performance Materials).

In accordance with the various embodiments, the amount of each of the at least one film-forming aminiosilicone polymer is from about 0.01 to about 5 wt. %, or from about 0.03 to about 4 wt. %, or from about 05 to about 3 wt. %, or from about 0.06% to about 2% or any suitable combination, sub-combination, range, or sub-range thereof by weight, based on the weight of the composition. One of ordinary skill in the art, however, will appreciate that other ranges are within the scope of the invention.

Thus, any one of the at least one film-forming aminiosilicone polymer is present, by weight, based on the total weight of the second phase of the hair treatment composition, from about 0.01, 0.02, 0.03, 0.04, 0.05, 0.06, 0.07, 0.08, 0.09, 0.1, 0.15 0.2, 0.25, 0.3, 0.35, 0.4, 0.45, 0.5, 0.6, 0.7, 0.8, 0.9, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3 to about 5 wt. %, including increments and ranges therein and there between.

Silicone Oil

The at least one silicone oil of the present disclosure may be selected from polyalkylsiloxanes, polyarylsiloxanes, polyalkarylsiloxanes, polyestersiloxanes, polyphenylsilicones, and a mixture thereof.

The term "silicone oil" is interchangeable with the terms "polysiloxane" and "polysiloxane oil." For purposes of the instant disclosure, "amino silicones" are not considered a "silicone oil." Instead, amino silicones form an independent category of component that may optionally be included in the hair treatment compositions. A more detailed definition and non-limiting examples of amino silicones are provided later, under the heading "Amino Silicone."

Non-limiting examples of silicone oils include polyalkylsiloxanes, polyarylsiloxanes, polyalkarylsiloxanes, polyestersiloxanes, polyphenylsiloxanes and a mixture thereof. In some instances, the silicone oil is preferably water insoluble at room temperature.

Representative examples of non-volatile, non-phenyl silicone oils which may be mentioned include cyclopentasiloxane, polydimethylsiloxanes; alkyl dimethicones; vinylmethyl methicones; and also silicones modified with aliphatic groups. It should be noted that "dimethicone" (INCI name) corresponds to a poly(dimethylsiloxane) (chemical name), which is particularly preferred in some instances.

The silicone oils are preferably chosen from non-volatile dimethicone oils. In particular, these oils can be chosen from the following non-volatile oils:

polydimethylsiloxanes (PDMSs),

PDMSs comprising aliphatic groups, in particular alkyl or alkoxy groups, which are pendent and/or at the end of the silicone chain, these groups each comprising from 2 to 24 carbon atoms. By way of example, mention may be made of the cetyl dimethicone sold under the commercial reference Abil Wax 9801 from Evonik Goldschmidt, PDMSs comprising aliphatic groups, or functional groups such as hydroxyl, thiol and/or amine groups, polyalkylmethylsiloxanes substituted with functional groups such as hydroxyl and thiol groups, polysiloxanes modified with fatty acids, fatty alcohols or polyoxyalkylenes, and mixtures thereof.

Preferably, non-volatile and non-phenyl silicone oils are chosen from polydimethylsiloxanes; alkyl dimethicones and also PDMSs comprising aliphatic groups, in particular $C_2$-$C_{24}$ alkyl groups.

The silicone oil may be chosen from silicones of the following formula:

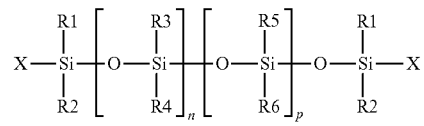

in which:

$R_1$, $R_2$, $R_5$ and $R_6$ are, together or separately, an alkyl radical containing 1 to 6 carbon atoms, $R_3$ and $R_4$ are, together or separately, an alkyl radical containing from 1 to 6 carbon atoms, a vinyl radical, or a hydroxyl radical, X is an alkyl radical containing from 1 to 6 carbon atoms, or a hydroxyl radical, n and p are integers chosen so as to have a fluid compound, in particular of which the viscosity at 25° C. is between 1 centistokes (cSt) and 1,000,000 (cSt).

As non-volatile non-phenyl silicone oils which can be used according to the invention, mention may be made of those for which:

the substituents $R_1$ to $R_6$ and X represent a methyl group, and p and n are such that the viscosity is 500 000 cSt, for example the product sold under the name SE30 by the company General Electric, the product sold under the name AK 500000 by the company Wacker, the product sold under the name Mirasil DM 500 000 by the company Bluestar, and the product sold under the name Dow Corning 200 Fluid 500 000 cSt by the company Dow Corning, the substituents $R_1$ to $R_6$ and X represent a methyl group, and p and n are such that the viscosity is 60 000 cSt, for example the product sold under the name Dow Corning 200 Fluid 60 000 CS by the company Dow Corning, and the product sold under the name Wacker Belsil DM 60 000 by the company Wacker, the substituents $R_1$ to $R_6$ and X represent a methyl group, and p and n are such that the viscosity is 100 cSt or 350 cSt, for example the products sold respectively under the names Belsil DM100 and Dow Corning 200 Fluid 350 CS by the company Dow Corning, the substituents $R_1$ to $R_6$ represent a methyl group, the group X represents a hydroxyl group, and n and p are such that the viscosity is 700 cSt, for example the product sold under the name Baysilone Fluid T0.7 by the company Momentive.

In some embodiments, it is preferable that the hair treatment compositions include two or more silicone oils, for example, two or more silicone oils selected from polyalkylsiloxanes, polyarylsiloxanes, polyalkarylsiloxanes, polyestersiloxanes, and a mixture thereof. In some instances, the two or more silicone oils are preferably two or more silicone oils selected from polyalkylsiloxanes (e.g., dimethicones) and cyclopentasiloxane. It is especially useful to include two or more silicone oils wherein at least one silicone oil has a viscosity of about 1 to 1000 centistokes and at least one silicone oil has a viscosity greater than 1000 to about 1,000,000 centistokes at 25° C. Centistokes is a standard unit used in the silicone industry for characterizing silicone oils because it is a representation of cinematic viscosity, which provides a better description of the behavior of silicone oils, as opposed to a dynamic viscosity (often represented by mPa·s). The viscosity of the silicone oils can be determined by methods known in the art, for example, using the Stokes viscosity or even a rotational viscometer.

The silicone oils having a viscosity of about 5 to 1000 cSt, may also have a viscosity of about 50 to about 1000 cSt, about 100 to about 1000 cSt, about 50 to about 750 cSt, about 100 to about 750 cSt, about 50 to about 500 cSt, about 100 to about 500 cSt, about 150 to about 500 cSt, about 200 to about 500 cSt, or about 350 cSt, including all ranges and subranges there between.

The total amount of all silicone oil(s) (except for the optional aminosilicone, which is not considered a silicone oil according to the instant disclosure) in the second phase of the hair treatment compositions can vary but is typically about 60 to about 99 wt. %, based on the total weight of the second phase or hair treatment composition. In some instances, the total amount of silicone oil(s) may be about 70 to about 98 wt. %, about 80 to about 98 wt. %, about 80 to about 98 wt. %, about 85 to about 98 wt. %, or about 90 to about 98 wt. %, based on the total weight of the second phase, including all ranges and subranges there between.

The total amount of all silicone oil(s) (except for the optional aminosilicone, which is not considered a silicone oil according to the instant disclosure) in the hair treatment compositions can vary but is typically about 10 to about 50 wt. %, based on the total weight of the hair treatment composition. In some instances, the total amount of silicone oil(s) may be about 12 to about 45 wt. %, about 15 to about 40 wt. %, about 15 to about 35 wt. %, about 15 to about 30 wt. %, about 15 to about 28 wt. %, about 15 to about 25 wt. %, or about 18 to about 25 wt. %, based on the total weight of the hair treatment composition, including all ranges and subranges there between.

Non-Silicone Oils

The at least one non-silicone oil includes, for example, fluoro oils, hydrocarbon-based oils, etc. The term "oil" means any fatty substance which is in liquid form at room temperature (20-25° C.) and at atmospheric pressure (760 mmHg). Often, at least one of the oils in the cosmetic composition is part of an oily phase. An "oily phase" is a phase comprising at least one oil that may include additional liposoluble and lipophilic ingredients and the fatty substances. The oily phase can be combined with an aqueous phase in an emulsion. Oil that is suitable for use herein may be volatile or non-volatile. The term "volatile oil" relates to oil that is capable of evaporating on contact with the skin or a keratin fiber in less than one hour, at room temperature and atmospheric pressure. The volatile oil(s) are liquid at room temperature and have a non-zero vapor pressure, at room temperature and atmospheric pressure, ranging in particular from 0.13 Pa to 40 000 Pa (10-3 to 300 mmHg). The term "non-volatile oil" relates to oil which remains on the skin or the keratin fiber, at room temperature and atmospheric pressure, for at least several hours and which in particular has a vapor pressure of less than 10-3 mmHg (0.13 Pa).

The term "fluoro oil" relates to oil comprising at least one fluorine atom. The term "hydrocarbon-based oil" relates to oil comprising mainly hydrogen and carbon atoms. Hydrocarbon-based oil may be animal hydrocarbon-based oil, plant hydrocarbon-based oil, mineral hydrocarbon-based oil or a synthetic hydrocarbon-based oil. Further, suitable oil may be a mineral hydrocarbon-based oil, a plant hydrocarbon-based oil, or a synthetic hydrocarbon-based oil.

Fluoro Oils

The one or more fluoro oil may be selected from the group consisting of perfluoromethylcyclopentane, perfluoro-1,3-dimethylcyclohexane, dodecafluoropentane, tetradecafluorohexane, bromoperfluorooctyl, nonafluoromethoxybutane, nonafluoroethoxyisobutane and 4-trifluoromethylperfluoromorpholine. Volatile fluoro oils, such as nonafluoromethoxybutane, decafluoropentane, tetradecafluorohexane, dodecafluoropentane, may also be used.

Hydrocarbon-Based Oils

The one or more hydrocarbon-based oils may be a saturated hydrocarbon, an unsaturated hydrocarbon, lipids, triglycerides, a natural oil, and/or a synthetic oil. In some embodiments, the compositions include a synthetic oil selected from the group consisting of hydrogenated polyisobutene and hydrogenated polydecene.

The hydrocarbon-based oil may be a non-volatile hydrocarbon-based, such as:

(i) hydrocarbon-based oils of plant origin, such as glyceride triesters, which are generally triesters of fatty acids and of glycerol, the fatty acids of which can have varied chain lengths from $C_4$ to $C_{24}$, it being possible for these chains to be saturated or unsaturated and linear or branched; these oils are in particular wheat germ oil, sunflower oil, grape seed oil, sesame oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin seed oil, marrow oil, blackcurrant oil, evening primrose oil, millet oil, barley oil, quinoa oil, rye oil, safflower oil, candlenut oil, passionflower oil, and musk rose oil.

(ii) synthetic ethers containing from 10 to 40 carbon atoms;

(iii) linear or branched hydrocarbons of mineral or synthetic origin, such as petroleum jelly, polydecenes, hydrogenated polyisobutene such as Parleam, and 4 0 squalane;

(iv) synthetic esters, for instance oils of formula RCOOR' in which R represents a linear or branched fatty acid residue containing from 1 to 40 carbon atoms and R' represents a hydrocarbon-based chain that is especially branched, containing from 1 to 40 carbon atoms on condition that R+R' is 10, for instance Purcellin oil (cetearyl octanoate), isopropyl myristate, isopropyl palmitate, $C_{12}$-$C_{15}$ alkyl benzoate, such as the product sold under the trade name Finsolv TN® or Witconol TN® by Witco or Tegosoft TN® by Evonik Goldschmidt, 2-ethylphenyl benzoate, such as the commercial product sold under the name X-Tend 226 by ISP, isopropyl lanolate, hexyl laurate, diisopropyl adipate, isononyl isononanoate, oleyl erucate, 2-ethylhexyl palmitate, isostearyl isostearate, diisopropyl sebacate, such as the product sold under the name of "Dub Dis" by Stearinerie Dubois, octanoates, decanoates or ricinoleates of alcohols or polyalcohols, such as propylene glycol dioctanoate; hydroxylated esters, such as isostearyl lactate or diisostearyl malate; and pentaerythritol esters; citrates or tartrates, such as di(linear $C_{12}$-$C_{13}$ alkyl) tartrates, such as those sold under the name Cosmacol ETI by Enichem Augusta Industriale, and also di(linear $C_{14}$-$C_{15}$ alkyl) tartrates, such as those sold under the name Cosmacol ETL® by the same company; or acetates;

(v) fatty alcohols that are liquid at room temperature, containing a branched and/or unsaturated carbon-based chain containing from 12 to 26 carbon atoms, for instance octyldodecanol, isostearyl alcohol, oleyl alcohol, 2-hexyl-decanol, 2-butyloctanol or 2-undecylpentadecanol;

(vi) higher fatty acids, such as oleic acid, linoleic acid or linolenic acid;

(vii) carbonates, such as dicaprylyl carbonate, such as the product sold under the name Cetiol CC by Cognis;

(viii) fatty amides, such as isopropyl N-lauroyl sarcosinate, such as the product sold under the trade name Eldew SL 205@ from Ajinomoto; and (ix) essential oils selected from the group consisting of sunflower oil, sesame oil, peppermint oil, macadamia nut oil, tea tree oil, evening primrose oil, sage oil, rosemary oil, coriander oil, thyme oil, pimento berries oil, rose oil, anise oil, balsam oil, bergamot oil, rosewood oil, cedar oil, chamomile oil, sage oil, clary sage oil, clove oil, cypress oil, eucalyptus oil, fennel oil, sea fennel oil, frankincense oil, geranium oil, ginger oil, grapefruit oil, jasmine oil, juniper oil, lavender oil, lemon oil, lemongrass oil, lime oil, mandarin oil, marjoram oil, myrrh oil, neroli oil, orange oil, patchouli oil, pepper oil, black pepper oil, petitgrain oil, pine oil, rose otto oil, rosemary oil, sandalwood oil, spearmint oil, spikenard oil, vetiver oil, wintergreen oil, and ylang ylang.

In certain instances, the non-volatile hydrocarbon-based oils are glyceride triesters and in particular to caprylic/capric acid triglycerides, synthetic esters and in particular isononyl isononanoate, oleyl erucate, $C_{12}$-$C_{15}$ alkyl benzoate, 2-ethylphenyl benzoate and fatty alcohols, such as octyldodecanol.

As volatile hydrocarbon-based oils, mention is made of hydrocarbon-based oils containing from 8 to 16 carbon atoms and in particular of branched $C_8$-$C_{16}$ alkanes, such as $C_8$-$C_{16}$ isoalkanes of petroleum origin (also known as isoparaffins), such as isododecane (also known as 2,2,4,4,6-pentamethylheptane), isodecane or isohexadecane, the oils sold under the Isopar or Permethyl trade names, branched C $C_8$-$C_{16}$ esters, and isohexyl neopentanoate.

Organic Solvents

The hair-treatment compositions or second phase of the hair treatment compositions may optionally include at least one organic solvent (non-silicone solvents).

Non-limiting examples of organic solvents include, for example, glycerin, alcohols (for example, $C_{1-15}$, $C_{1-10}$, or $C_{1-6}$ alcohols), organic solvents, polyols (polyhydric alcohols), glycols (e.g., butylene glycol, caprylyl glycol, etc.), and a mixture thereof.

Non-limiting examples of organic solvents include monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of organic solvents include alkanediols such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount organic solvent(s) in the second phase or hair treatment composition, if present, can vary but is typically about 0.1 to about 10 wt. %, based on the total weight of the second phase or hair treatment composition. In some cases, the total amount of water-soluble solvent(s) is about 0.1 to about 8 wt. %, about 0.1 to about 6 wt. %, about 0.1 to about 0.5 to about 10 wt. %, about 0.5 to about 8 wt. %, about 0.5 to about 6 wt. %, about 0.5 to about 5 wt. %, about 1 wt. %, about 2 wt. %, about 3 wt. %, or about 4 wt. %, including all ranges and subranges there between.

In an embodiment, the second phase is substantially free of water.

Other Components

In one or more embodiments, the hair treatment compositions and first and second phases described herein may contain one or more additional ingredients. Examples include, but are not limited to oils (natural or plant-based or synthetic, non-silicone oils), surfactants, emulsifiers, cationic conditioning agents, aminosilicones, non-silicone organic solvents, film formers, other polymers, fragrance and preservatives. Additional details regarding such additional ingredients follows below.

Preservatives

One or more preservatives may be included in the compositions and phases described herein for treating hair. Suitable preservatives include, but are not limited to, glycerin containing compounds (e.g., glycerin or ethylhexylglycerin or phenoxyethanol), benzyl alcohol, parabens (methylparaben, ethylparaben, propylparaben, butylparaben, isobutylparaben, etc.), sodium benzoate, ethylenediaminetetraacetic acid (EDTA), potassium sorbate, and/or grapefruit seed extract, or combinations thereof. More than one preservative may be included in the composition. Other preservatives are known in the cosmetics industries and include salicylic acid, DMDM Hydantoin, Formaldahyde, Chlorphenism, Triclosan, Imidazolidinyl Urea, Diazolidinyl Urea, Sorbic Acid, Methylisothiazolinone, Sodium Dehydroacetate, Dehydroacetic Acid, Quaternium-15, Stearalkonium Chloride, Zinc Pyrithione, Sodium Metabisulfite, 2-Bromo-2-Nitropropane, Chlorhexidine Digluconate, Polyaminopropyl biguanide, Benzalkonium Chloride, Sodium Sulfite, Sodium Salicylate, Citric Acid, Neem Oil, Essential Oils (various), Lactic Acid, and Vitamin E (tocopherol).

The total amount of the one or more preservatives, when present, may vary. In some cases, the total amount of the one or more preservatives is about 0.01 to about 5 wt. %, about 0.01 to about 4 wt. %, about 0.15 to about 1 wt. %, or about 1 to about 3 wt. %, based on the total weight of the composition.

Emulsifiers

Emulsifiers as referred to herein, may also include co-emulsifiers. Emulsifiers may be chosen from nonionic surfactants such as alkoxylated fatty alcohols, fatty alcohols, polyglycerol esters of fatty acids, alkyl polyglycosides, polysorbates, amino acid emulsifiers, and alkyl amine oxides.

Suitable components, such as those listed in the instant disclosure (including those listed above), may be included or excluded from the hair styling compositions depending on the specific combination of other components, the form of the compositions, and/or the use of the formulation (e.g., hair spray, cream, paste, conditioner, etc.).

Ratio of First Phase to Second Phase

In forming the hair treatment composition or system, the first phase (aqueous) can be combined with the second phase (oil) in a weight ratio ranging from about 2:0.5 to about 5:1 or from about 2:1 to about 4:1 or from about 2:1 to about 3:1, including all ranges and sub-ranges therebetween.

Methods

Another aspect of the invention pertains to methods of using the hair treatment compositions described herein. The methods generally comprise applying any of the hair treatment compositions described to hair. The hair treatment compositions may be useful in a variety of settings, and either for treated or untreated hair. Use on treated hair can include chemically relaxed hair. The hair treatment composition may be applied post relaxer but before neutralizing shampoo, after neutralizing shampoo, in or as a conditioner, or as a leave in treatment after the relaxation process. Use on untreated hair may include as part of a shampoo, part of a conditioner, as a pre-treatment, or after washing the hair as a leave-in treatment.

Methods of treating hair according to the disclosure may include applying a hair treatment composition of the instant disclosure to the hair (wet, damp, or dry hair), allowing the hair treatment to remain on the hair for a sufficient amount of time, and rinsing the hair treatment composition from the hair. The hair treatment composition may be applied to the hair before, during, or after other hair treatment compositions (e.g., a chemical relaxer composition, a shampoo, a conditioner, a lotion, a gel, etc.).

As mentioned previously, the hair treatment compositions are particularly useful for treating chemically treated hair. In some cases, a hair treatment composition is applied to the hair shortly after a chemical treatment composition is rinsed from the hair (e.g., within about 5, 10, 15, 20, or 30 minutes from when the chemical treatment composition is rinsed from the hair), while the hair is still wet or damp. The hair treatment composition may be allowed to remain on the hair for a period of time, for example from about a few seconds (1, 3, 5, or 10 seconds) to about 10, 20, or 30 minutes, or longer. In some cases, the hair treatment composition is applied to the chemically treated hair shortly after a chemical treatment composition is rinsed from the hair; and after applying the hair treatment composition, the hair is subsequently treated with a shampoo and/or a conditioner, or a conditioning shampoo (all-in-one shampoo/conditioner). The hair treatment composition may be rinsed from the hair prior to application of a shampoo and/or a conditioner, or a conditioning shampoo, or it may be allowed to remain on the hair during shampooing and/or conditioning and rinsed from the hair with the shampoo or the conditioner, or with the conditioning shampoo. For example, the hair treatment composition may be applied to the hair and without rinsing the hair treatment from the hair, a shampoo (or conditioner or conditioning shampoo) is subsequently applied to the hair (layered onto the hair treatment composition already applied to the hair). Both compositions (the hair treatment composition and the shampoo, conditioner, or conditioning shampoo) are rinsed from the hair together.

Moreover, the hair treatment composition may be combined with a shampoo and/or a conditioner, or with a conditioning shampoo, prior to application to the hair. Combining the hair treatment compositions with one or more additional hair treatment compositions (e.g., a shampoo, a conditioner, a conditioning shampoo, a rinse, etc.). For instance, the hair treatment composition may be mixed with a shampoo (or conditioner or conditioning shampoo) prior to application to the hair. In this case, the mixture of the shampoo (or conditioner or conditioning shampoo) and the hair treatment composition are simultaneously applied to the hair during the cleansing and/or conditioning process and simultaneously rinsed from the hair. Alternatively, the hair treatment composition may be layered on top of (or lathered into) hair to which a shampoo (or conditioner or conditioning shampoo) has already been applied or vice versa. In this case, the hair treatment composition may be applied to the hair first and without rinsing it from the hair, a shampoo (or conditioner or conditioning shampoo) is then subsequently applied to the hair. Alternatively, the shampoo (or conditioner or conditioning shampoo) may be first applied to the hair and without rinsing the shampoo (or conditioner or conditioning shampoo) from the hair, the hair treatment composition is also applied to the hair. Then, the compositions are simultaneously rinsed from the hair.

Described above is the individual application of a hair treatment composition or the combined or layered application of a hair treatment composition with another composition (e.g., a shampoo, conditioner, conditioning shampoo, etc.). In some cases, a hair treatment composition is individually applied to the hair and also combined or layered with another composition (e.g., a shampoo, conditioner, conditioning shampoo, etc.) that is also applied to the hair. For example, a hair treatment composition may be applied to the hair. Subsequently, with or without rinsing the hair treatment composition from the hair, another composition (e.g., a shampoo, conditioner, conditioning shampoo, etc.) in which the hair treatment composition has been mixed may be applied to the hair.

When combined with another composition (e.g., a shampoo, conditioner, conditioning shampoo, etc.), the hair treatment composition may be mixed with or used with in a ratio of about 1:10 to about 10:1, about 1:5 to about 5:1, about 1:3 to about 3:1, about 1:2 to about 2:1, about 1:1 to about 4:1, about 1:1 to about 3:1, or about 1:1 to about 2:1 (hair treatment composition of the instant disclosure:another composition).

The hair treatment compositions may be allowed to remain on the hair for a minimum amount of time before being rinsed from the hair, but allowing the hair treatment composition to remain on the hair for an extended period of time is not needed. Conveniently, the hair treatment compositions can be applied and allowed to remain on the hair for a period of time that is typical for regular shampooing and/or conditioning. For example, the hair treatment composition (whether combined with another hair treatment composition such as a shampoo or conditioner) may be applied to the hair and allowed to remain on the hair for a few seconds (1, 2, 3, 5, or 10 seconds) up to about 1, 2, 5, 10, 20, or 30 minutes, or longer.

When the hair treatment composition is not applied to the hair, simultaneously with another composition (e.g., a shampoo, conditioner, conditioning shampoo, etc.), the hair treatment composition may be applied to the hair immediately after or before the hair is treated with another composition (e.g., a shampoo, conditioner, conditioning shampoo, etc.). For example, the hair treatment compositions may be applied to the hair within about 1, 2, 5, 10, or 20 minutes before or after another composition is applied to the hair.

Kits

The hair treatment compositions of the instant disclosure may be incorporated into a kit. For example, the kits may include at least one hair treatment composition according to the instant disclosure or the aqueous phase and the oil phase according to the instant disclosure as separate components and one or more additional hair treatment compositions, for example, a hair relaxer composition, a shampoo, a conditioner, etc.

The various hair treatment compositions and/or the aqueous phase and oil phase according to the instant disclosure are separately contained in the kits. In some instances, the kits include one or more hair treatment compositions (according to the instant disclosure) or the aqueous phase and the oil phase according to the instant disclosure, a shampoo, and/or a conditioner, all of which are separately contained. The kits may also include one or more hair treatment compositions (according the instant disclosure) or the aqueous phase and the oil phase according to the instant disclosure, a chemical relaxer composition, and optionally a shampoo and/or a conditioner. Instructions, mixing components, brushes, gloves, measuring tools, etc., may also be included in the kits.

Implementation of the present disclosure is provided by way of the following examples. The examples serve to illustrate the technology without being limiting in nature.

EXAMPLES

The following Examples are intended to be non-restrictive and explanatory only. The ingredient amounts in the compositions/formulas described below are expressed in % by weight, based on the total weight of the composition.

Several formulas were produced having the ingredients as listed in the tables below. The balance of all formulas was water.

Example I: Composition

TABLE 1

| | US INCI NAME OF INGREDIENTS | Formula X Wt. % (Active) |
|---|---|---|
| First Phase A (aqueous) | MALEIC ACID | 1.3 |
| | ETHANOLAMINE | 0.68 |
| | AMINOPROPYL TRIETHOXYSILANE | 1.88 |
| | POLYQUATERNIUM-6 | 0.3 |
| | DIPROPYLENE GLYCOL | 0.23 |
| | HEXYLENE GLYCOL | 1.13 |
| | BUTYLENE GLYCOL | 1.13 |
| | CAPRYLYL GLYCOL | 0.4 |
| | PHENOXYETHANOL | 0.6 |
| | WATER | 67.8 |
| Second Phase B (oil) | POLYSILICONE-29 | 0.08 |
| | CYCLOPENTASILOXANE | 21.5 |
| | DIMETHICONOL | 1.7 |
| | OLEA EUROPAEA (OLIVE) FRUIT OIL | 1.3 |

Example II: In Viva Testing (on Hair Swatches)

Samples of various formulations of the aqueous phase, the oil phase, and the aqueous and oil phases together were tested on hair swatches to. The samples were applied onto hair swatches and the treated swatches were then placed in a humidity chamber for 24 hours at 25° C. and 80% relative humidity. Each swatch was visually and sensorially assessed and the width of each swatch at the middle and bottom (cm) using a digital caliper was measured. The width measurements can be correlated with the degree of frizziness. The measurements can also be correlated to the spread of the hair which could indicate the volumized or poofy (puffed up) appearance of the hair. However, it should be noted that the hair can have less spread or width but at the same time, visually exhibit frizziness.

Example IIA: Phases

TABLE 2

| Aqueous (Water) Phases | | |
|---|---|---|
| Aqueous Phase | US INCI NAME OF INGREDIENTS | Wt. % (Active) |
| A | Polyquaternium-6 | 0.40% |
| | Aminopropyl triethoxysilane | 2.50% |
| | Deionized Water | QS 100% |
| B | Hexylene Glycol | 1.50% |
| | Butylene Glycol | 1.50% |
| | Deionized Water | QS 100% |
| C | Maleic Acid | 1.8% |
| | Ethanolamine | 0.90% |
| | Deionized Water | QS 100% |
| D | Polyquaternium-6 | 0.40% |
| | Aminopropyl triethoxysilane | 2.50% |
| | Hexylene Glycol | 1.50% |
| | Butylene Glycol | 1.50% |
| | Deionized Water | QS 100% |
| E | Polyquaternium-6 | 0.40% |
| | Aminopropyl triethoxysilane | 2.50% |
| | Maleic Acid (30% Solution) | 1.8% |

TABLE 2-continued

Aqueous (Water) Phases

| Aqueous Phase | US INCI NAME OF INGREDIENTS | Wt. % (Active) |
|---|---|---|
| | Ethanolamine | 0.90% |
| | Deionized Water | QS 100% |
| F | Polyquaternium-6 | 0.40% |
| | Aminopropyl triethoxysilane | 2.50% |
| | Maleic Acid | 1.80% |
| | Ethanolamine | 0.90% |
| | Hexylene Glycol | 1.50% |
| | Butylene Glycol | 1.50% |
| | Deionized Water | Q.S. 100% |
| G | Maleic Acid | 1.80% |
| | Ethanolamine | 0.90% |
| | Hexylene Glycol | 1.50% |
| | Butylene Glycol | 1.50% |
| | Deionized Water | QS 100% |

The process of making the aqueous phase was as follows:
a. Add water to beaker; begin mixing using a Rayneri mixer with propeller blade attachment.
b. Add each raw material or ingredient, one at a time. Mix well between each addition.

TABLE 3

Oil Phases

| Oil Phase | US INCI NAME OF INGREDIENTS | Wt. % (Active) |
|---|---|---|
| H1 | DIMETHICONOL | 6.8% |
| | CYCLOPENTASILOXANE (100% active) | 86.2% |
| | Polysilicone-29 | 0.3% |
| | Olive Oil (100% active) | 5% |
| | Dipropylene glycol | 0.9% |
| | Water | 0.8% |
| | Total | 100.00% |
| H2 | DIMETHICONOL | 7.2% |
| | CYCLOPENTASILOXANE | 90.8% |
| | Polysilicone-29 | 0.15% |
| | Olive Oil | 1% |
| | Dipropylene glycol | 0.45% |
| | Water | 0.4% |
| | Total | 100% |
| H3 | DIMETHICONOL | 7.2% |
| | CYCLOPENTASILOXANE | 90.8% |
| | Olive Oil | 2% |
| | Total | 100% |

The process of making the oil phase was as follows:
a. Add each RM one at a time while mixing using a Rayneri mixer with propeller blade attachment.

Example IIB: Assessments of Hair Swatches

Hair Treatment Protocol:
Each test swatch (Caucasian Curl Type 4) was treated according to the following:
1. The swatch was shampooed with a convention cleansing shampoo by lathering the shampoo on the hair for 30 seconds (1 ml per 2.5 gram hair swatch); the swatch was then rinsed with water.
2. Excess water was removed by running the fingers through the hair.
3. Each treatment was applied on the shampooed swatch and carefully worked through the hair (bi-phase treatment=1 g/2.5 g swatch; aqueous phase treatment=0.75 g/2.5 g swatch; oil phase treatment=0.25 g/2.5 g swatch.
4. The swatches were allowed to air dry.

TABLE 4

Assessment of Hair Treated with Oil Phase and Control

| BEFORE HUMIDITY EXPOSURE(DRY) | AFTER HUMIDITY EXPOSURE* | % CHANGE** |
|---|---|---|
| Oil Phase only, Control H2 | | |
| 1.6 cm (m) | 2.4 cm (m) | 50.0% |
| 1.9 cm (b) | 2.7 cm (b) | 42.1% |
| | Hair appeared and felt greasy | |
| Control, Z (cleansed swatch; no treatment) | | |
| 5.7 cm (m) | 7.1 cm (m) | 24.6% |
| 4.9 cm (b) | 8.1 cm (b) | 65.3% |
| | Very frizzy | |

*All swatches were placed in humidity chamber for 24 hours, at 25° C. and 80% relative humidity
**percent change is calculated by taking the difference in width measurements of each swatch before and after humidity exposure divided by the width measurement before humidity exposure

TABLE 5

Assessment of Hair Treated with Aqueous Phase Only (from Table 2); Comparison of Various formulations of the Aqueous Phase and to Control

| BEFORE HUMIDITY EXPOSURE(DRY) | AFTER HUMIDITY EXPOSURE* | % CHANGE** |
|---|---|---|
| I (Aqueous Phase A) | | |
| 2.6 cm (m) | 4.5 cm (m) | 73.1% |
| 2.7 cm (b) | 4.0 cm (b) | 48.1% |
| A little crunchy; sealed ends | A little stiff; sealed ends and less poofy*** than Z/J/K | |
| J (Aqueous Phase B) | | |
| 3.9 cm (m) | 5.7 cm (m) | 46.2% |
| 4.6 cm (b) | 5.9 cm (b) | 28.3% |
| Frizzy, poofy***; ends not sealed | Natural feel but frizzy | |
| K (Aqueous Phase C) | | |
| 4.2 cm (m) | 5.2 cm (m) | 23.8% |
| 3.3 cm (b) | 4.8 cm (b) | 45.5% |
| A little stiff; I better than K and K better than J (frizz-wise). | Sealed ends and natural feel but frizzy | |
| L (Aqueous Phase D) | | |
| 2.5 cm (m) | 3.0 cm (m) | 20.0% |
| 2.0 cm (b) | 4.1 cm (b) | 100+% |
| A little crunchy; very sleek; sealed ends | A little stiff | |
| M (Aqueous Phase E) | | |
| 2.6 cm (m) | 4.9 cm (m) | 88.5% |
| 2.6 cm (b) | 5.4 cm (b) | 100+% |
| A little crunchy; ends are almost sealed; good visual appearance | | |
| N (Aqueous Phase F) | | |
| 2.6 cm (m) | 3.0 cm (m) | 15.3% |
| 2.5 cm (b) | 3.4 cm (b) | 36.0% |
| A little crunchy; sealed ends. | Least frizzy and poofy; sealed ends; nice | |

TABLE 5-continued

Assessment of Hair Treated with Aqueous Phase Only
(from Table 2); Comparison of Various
formulations of the Aqueous Phase and to Control

| BEFORE HUMIDITY EXPOSURE(DRY) | AFTER HUMIDITY EXPOSURE* | % CHANGE** |
|---|---|---|
| Best visual appearance - good frizz control with nice curl pattern and volume | curl pattern Best visual appearance; gave the best shine | |
| O (Aqueous Phase G) | | |
| 3.7 cm (m) | 6.1 cm (m) | 64.8% |
| 4.2 cm (b) | 6.4 cm (b) | 52.3% |
| More natural feel; sealed ends; less frizz control than N | Very frizzy | |

*All swatches were placed in humidity chamber for 24 hours, at 25° C. and 80% relative humidity
**percent change is calculated by taking the difference in width measurements of each swatch before and after humidity exposure divided by the width measurement before humidity exposure
***poofy means puffed up or having too much volume or more spread out Summary of Table 5 results: Treatment N (aqueous phase F) resulted in the lowest percent change in the width of the middle section of the swatch compared to the other treatments. Also, Treatment N (aqueous phase F) resulted in the lowest percent change in the width of the bottom section of the swatch compared to the other treatments, except for Treatment J. Treatment J had the lowest percent change in width but the treated swatch exhibited more frizziness compared to the swatch treated with Treatment N.

TABLE 6

Assessment of Hair Treated with Bi-phase (Oil Phase, H2, and Aqueous Phase from Table 2; (25% oil phase, 75% Aqueous Phase) Comparison of Various Combinations of the Aqueous Phase and the Oil Phase

| BEFORE HUMIDITY EXPOSURE(DRY) | AFTER HUMIDITY EXPOSURE* | % CHANGE** |
|---|---|---|
| Bi-Phase A | | |
| 2.9 cm (m) | 3.7 cm (m) | 27.6% |
| 1.4 cm (b) | 2.6 cm (b) | 85.7% |
| crunchy | crunchy | |
| Bi-Phase B | | |
| 4.2 cm (m) | 5.6 cm (m) | 33.3% |
| 4.5 cm (b) | 5.7 cm (b) | 26.7% |
| Ends are not sealed | Very frizzy, poofy and with fly-aways) | |
| Bi-Phase C | | |
| 4.6 cm (m) | 5.0 cm (m) | 8.7% |
| 3.4 cm (b) | 4.1 cm (b) | 20.6% |
| | Less poofy than B but frizzy | |
| Bi-Phase D | | |
| 1.6 cm (m) | 2.5 cm (m) | 56.3% |
| 1.2 cm (b) | 2.6 cm (b) | 100+% |
| Crunchy | A little crunchy; ends are apart | |
| Bi-Phase E | | |
| 4.1 cm (m) | 5.0 cm (m) | 21.9% |
| 3.5 cm (b) | 4.5 cm (b) | 28.6% |
| Stiff | A little stiff; poofy | |
| Bi-Phase F (invention) | | |
| 2.8 cm (m) | 3.8 cm (m) | 35.7% |
| 2.7 cm (b) | 4.1 cm (b) | 51.9% |
| A little stiff. Best visual appearance; more shine | Still has shine; nice curl pattern. Best visual appearance; more shine | |
| Bi-Phase G | | |
| 5.1 cm (m) | 5.8 cm (m) | 13.7% |
| 5.3 cm (b) | 6.8 cm (b) | 28.3% |
| Ends not sealed | Seems to be the most poofy | |

Figure 1B:
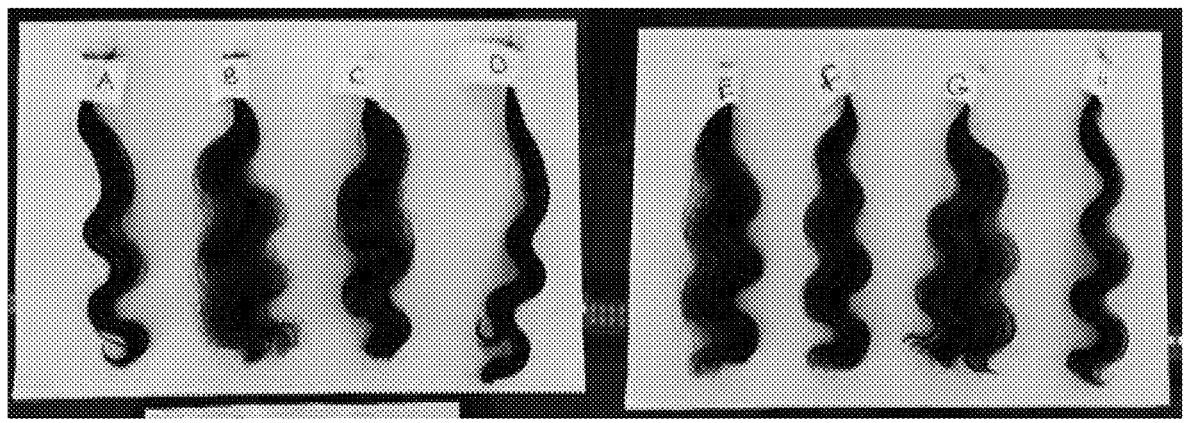
Figure 2:
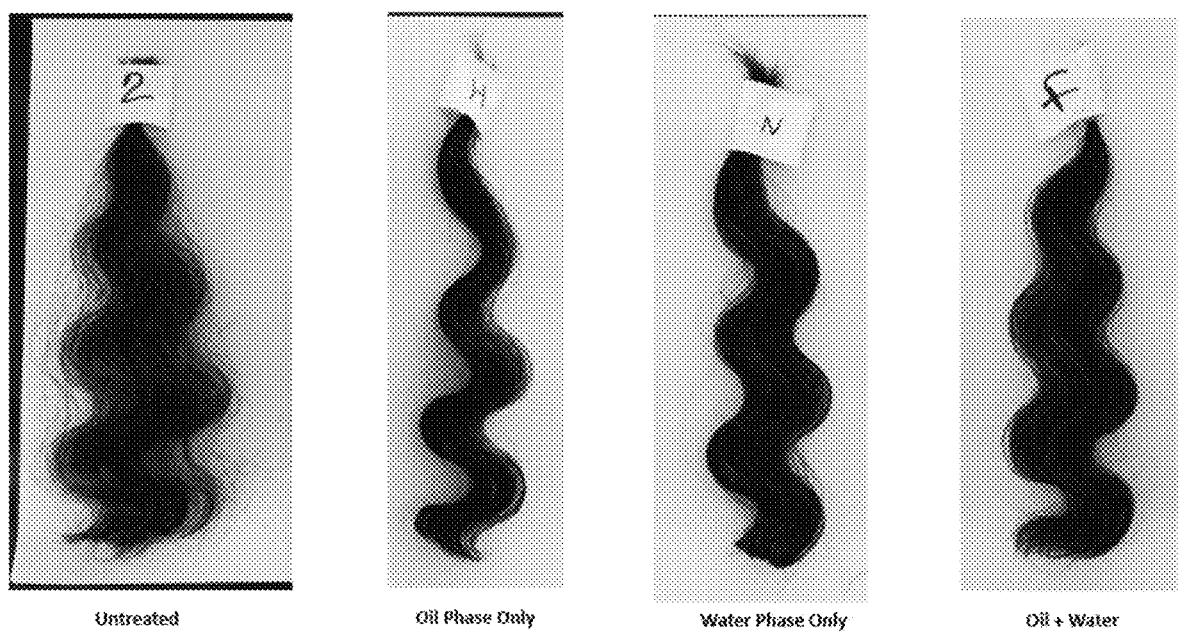
FIG. 2 includes pictures of a control hair swatch and hair swatches at high humidity condition after treating with an oil phase only, an aqueous phase only, and an inventive bi-phase composition (F); the high humidity condition refers to keeping the swatches for 24 hours at 80% relative humidity and at 25° C.

*All swatches were placed in humidity chamber for 24 hours, at 25° C. and 80% relative humidity
**percent change is calculated by taking the difference in width measurements of each swatch before and after humidity exposure divided by the width measurement before humidity exposure
***poofy means puffed up or having too much volume or more spread out Summary of Table 6 results: Treatment with the bi-phase treatment F resulted in a best visual appearance of the hair, more shine, very good curl pattern, and curl definition as compared to the hair treated with the other treatments, even if the percent change in width could have been higher compared to some of the other treatments which produced one or more of the less desirable effects such as stiffness, crunchiness, unsealed ends of the hair, more frizziness, too much volume and/or fly-aways at the ends, even when the percent change in width was less. This is evident from the images presented in FIGS. 1A and 1B and in FIG. 2 which shows swatches treated with Treatments H2 (oil phase), N (aqueous phase), and F (biphase—combination of oil phase H2 and aqueous phase N).

In particular, while some of the treatments showed lower percent changes in the width of the swatches compared to bi-phase treatment F, the swatches visually appeared to be very frizzy. For example, the percent changes for the swatches treated with the combination of the aqueous phase C, with an oil phase, H2, (Bi-Phase Treatment C) were lower compared to other percent changes but the swatches were visually found to be very frizzy.

Conclusion: It was found that while some swatches treated with the aqueous phases alone had less poofiness or less width, the treatments with the aqueous phases did not provide enough shine to the hair and the hair swatches generally felt more dry to the touch. On the other hand, while the treatment with the oil phase alone (Control H2) could provide shine to hair, treatment with the oil phase alone did not necessarily reduce the width of the swatches (% changes of 42 to 50%) and made the hair feel and look greasy. By combining the oil phase H with the aqueous phase N to form the bi-phase treatment F, the inventors discovered that the bi-phase treatment reduced the hair crunchiness, smoothened the flyaways, and provided shine, a very good curl pattern, curl definition, and the best visual appearance among all the swatches treated with the bi-phase compositions. At the same time, it was found that bi-phase treatment F provided softness to the hair. When swatch treated with the invention (bi-phase treatment F) exhibited the best visual appearance with respect to curl patterns, curl definition, and frizz control as compared to the swatches treated with Control, Z, oil phase H2 alone, and aqueous phase N alone (see FIG. 2).

In addition, the inventors surprisingly discovered that the cosmetic attributes provided by bi-phase treatment F such as frizz control and curl pattern and curl definition lasted even after exposing the hair to high humidity conditions, thereby conferring humidity-resistant properties to hair.

Thus, the combination of ingredients in the aqueous phase and in the oil phase to form bi-phase treatment F plus the right balance of the amount of the aqueous phase and of the oil phase resulted in the best overall performance by bi-phase treatment F with respect to the visual and sensorial attributes.

Example IV Performance Testing on Hair Swatches

Comparison of Swatches after 24 Hours at 80% Relative Humidity

TABLE 7

| Attributes | Untreated | Oil Phase, H2 | Aqueous Phase, F | Oil + Aqueous Phases (Bi-Phase F) |
|---|---|---|---|---|
| Anti-Frizz | − | +++ | ++ | +++ |
| Long-Lasting | − | ++ | ++ | +++ |
| Natural Feel | +++ | + | + | +++ |
| Shine | − | +++ | ++ | +++ |
| Smoothness | − | +++ | ++ | +++ |
| Curl Definition | − | ++ | +++ | +++ |
| Lightweight | − | + | +++ | +++ |

Key
− Unfavorable
+ Ok
++ Good
+++ Very good

The results in Table 7 above show that the swatches treated with the bi-phase treatment F had very good ratings with respect to all the attributes tested, which include visual and sensorial attributes, even after exposing the hair to high humidity conditions.

The foregoing description illustrates and describes the invention. The disclosure shows and describes only the preferred embodiments but it should be understood that the invention is capable to use in various other combinations, modifications, and environments and is capable of changes or modifications within the scope of the inventive concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" also relates to "mixtures thereof." Throughout the disclosure, if the term "a mixture thereof" is used, following a list of elements as shown in the following example where letters A-F represent the elements: "one or more elements selected from the group consisting of A, B, C, D, E, F, or mixtures thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, or mixtures thereof," it indicates that that one or more of A, B, C, D, and F may be included, one or more of a salt of A, a salt of B, a salt of C, a salt of D, a salt of E, and a salt of F may be included, or a mixture of any two of A, B, C, D, E, F, a salt of A, a salt of B, a salt of C, a salt of D, a salt of E, and a salt of F may be included.

The salts referred to throughout the disclosure may include salts having a counterion such as an alkali metal, alkaline earth metal, or ammonium counterion. This list of counterions, however, is non-limiting.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−1%, 2%, 3%, 4%, or 5% of the indicated number.

Some of the various categories of components identified for the hair-treatment compositions may overlap. In such cases where overlap may exist and the composition/product includes two overlapping components (or more than two overlapping components), an overlapping component does not represent more than one component. For example, a fatty acid may be defined as both a "fatty compound" and a "surfactant/emulsifier." If a particular composition/product includes both a fatty compound component and an emulsifier component, a single fatty acid can serve as only a fatty compound or a surfactant/emulsifier (a single fatty acid does not serve as both the fatty compound and the surfactant/emulsifier).

All percentages, parts and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically points 1, 2, 3, 4 and 5, as well as sub-ranges such as 2-5, 3-5, 2-3, 2-4, 1-4, etc.; and points of 1, 2, 3, 4, and 5 includes ranges and sub-ranges of 1-5, 2-5, 3-5, 2-3, 2-4, 1-4, etc.

All numbers herein are understood to be modified by "about," whether or not expressly stated. Additionally, all numbers are intended to represent exact figures as additional embodiments, whether or not modified by "about." For example, "an amount of about 1%" includes an amount of exactly 1%. As a further example, "an amount of 1%" includes an amount of about 1%. The term "about" is generally understood to encompass a range of +/−10% from the stated number, and is intended to cover amounts of +/−1%, 2%, 3%, 4%, 5%, 6%, 7%, 8%, 9%, and 10%.

The term "surfactants" includes salts of the surfactants even if not explicitly stated. In other words, whenever the disclosure refers to a surfactant, it is intended that salts of the surfactant are also encompassed to the extent such salts exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "substantially free" or "essentially free" as used herein means the specific material may be present in small amounts that do not materially affect the basic and novel characteristics of the claimed invention. For instance, there may be less than 2% by weight of a specific material added to a composition, based on the total weight of the compositions (provided that an amount of less than 2% by weight does not materially affect the basic and novel characteristics of the claimed invention. Similarly, the compositions may include less than 2 wt %, less than 1.5 wt %, less than 1 wt %, less than 0.5 wt %, less than 0.1 wt %, less than 0.05 wt %, or less than 0.01 wt %, or none of the specified material. Furthermore, all components that are positively set forth in the instant disclosure may be negatively excluded from the claims, e.g., a claimed composition may be "free," "essentially free" (or "substantially free") of one or more components that are positively set forth in the instant disclosure.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:
1. A hair treatment composition comprising:
   (a) a first phase comprising:
      at least one non-polymeric mono, di, or tricarboxylic acid, and/or a salt thereof, and a mixture thereof;
      at least one amine selected from diamines, polyamines, alkylamines, alkanolamines, and a mixture thereof;
      at least one cationic polymer;
      at least one alkoxysilane selected from 3-mercaptopropyltriethoxysilane and/or 3-aminopropyltriethoxysilane;
      at least one polyol; and
      water;
   and
   (b) a second phase comprising:
      Polysilicone-29; and
      at least one silicone oil;
   wherein the weight ratio of the first phase (a) to the second phase (b) ranges from about 2:0.5 to about 5:1.
2. The hair treatment composition of claim 1, wherein the at least one non-polymeric mono, di, or tricarboxylic acid, and/or a salt thereof, is a dicarboxylic acid and/or a salt thereof.
3. The hair treatment composition of claim 2, comprising at least one dicarboxylic acid and/or a salt thereof, selected from oxalic acid, malonic acid, malic acid, glutaric acid, citraconic acid, succinic acid, adipic acid, tartaric acid, fumaric acid, maleic acid, sebacic acid, azelaic acid, dodecanedioic acid, phthalic acid, isophthalic acid, terephthalic acid, 2,6-naphthalene dicarboxylic acid, their salts thereof, and a mixture thereof.

4. The hair treatment composition of claim 3, wherein the at least one dicarboxylic acid and/or a salt thereof is maleic acid, malonic acid, and/or a salt thereof, and a mixture thereof.
5. The hair treatment composition of claim 2, comprising at least one tricarboxylic acid and/or a salt thereof, wherein the at least one tricarboxylic acid and/or a salt thereof is selected from citric acid, isocitric acid, aconitric acid, propane-1,2,3-tricarboxylic acid, benzene-1,3,5-tricarboxylic acid, their salts thereof, and a mixture thereof.
6. The hair treatment composition of claim 5, wherein the at least one tricarboxylic acid and/or a salt thereof is citric acid, and a mixture thereof.
7. The hair treatment composition of claim 1 the at least one non-polymeric mono, di, or tricarboxylic acid and/or a salt thereof, is present in an amount of at least 0.5 to about 20 wt. % based on the total weight of the first phase of the hair treatment composition.
8. The hair treatment composition of claim 1 comprising at least one amine including one or more alkylamines and/or alkanolamines selected from the compounds of formula (II):

$NR_3R_4R_5$           (II)

wherein $R_3$, $R_4$ and $R_5$ are independently H, $C_1$-$C_{40}$ alkyl, $C_1$-$C_{40}$ monohydroxyalkyl or $C_2$-$C_{40}$ polyhydroxyalkyl, provided that at least one of $R_3$, $R_4$ and $R_5$ is an alkyl or mono or polyhydroxyalkyl.
9. The hair treatment composition of claim 8 comprising one or more alkanolamines selected from monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and a mixture thereof.
10. The hair treatment composition of claim 9 comprising monoethanolamine.
11. The hair treatment composition of claim 1, wherein the at least one amine is present in an amount of about 0.1 to about 20 wt. %, based on the total weight of the first phase of the hair treatment composition.
12. The hair treatment composition of claim 1, wherein the at least one cationic polymer is selected from poly (methacryloyloxyethyl trimethylammonium chloride), polyquaternium-37, quaternized cellulose derivatives, polyquaternium-4, polyquaternium-6, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof.
13. The hair treatment composition of claim 12, wherein the at least one cationic polymer is polyquaternium-6.
14. The hair treatment composition of claim 1, wherein the at least one cationic polymer is present in an amount of about 0.01 to about 10 wt. %, based on the total weight of the first phase of the hair treatment composition.
15. The hair-treatment composition of claim 1, wherein the at least one alkoxysilane is present in an amount of about 0.1 to about 20 wt. %, based on the total weight of the first phase of the hair-treatment composition.

16. The hair treatment composition of claim 1, wherein the at least one polyol is selected from hexylene glycol, butylene glycol, propylene glycol, dipropylene glycol, caprylyl glycol, glycerin, and a mixture thereof.

17. The hair treatment composition of claim 1, wherein the at least one polyol is present in an amount of about 0.1 to about 20 wt. %, based on the total weight of the first phase of the hair-treatment composition.

18. The hair treatment composition of claim 1, wherein the Polysilicone-29 is present in an amount from about 0.01% to about 5% by weight, based on the total weight of the second phase of the hair treatment composition.

19. The hair treatment composition of claim 1, wherein the at least one silicone oil is selected from polyalkylsiloxanes, polyarylsiloxanes, polyalkarylsiloxanes, polyestersiloxanes, polyphenylsiloxanes and a mixture thereof.

20. The composition of claim 1, wherein the weight ratio of the first phase (a) to the second phase (b) ranges from about 2:1 to about 4:1.

21. The composition of claim 1, wherein the composition has a bi-phasic appearance.

22. The composition of claim 1, wherein the composition is in a spray form.

23. The composition of claim 1, wherein the first phase or the second phase or both first and second phases are substantially free of emulsifiers.

24. A hair treatment composition comprising:
(a) a first phase comprising:
    about 0.6 to about 15 wt. % of at least one non-polymeric mono, di, or tricarboxylic acid, and/or a salt thereof and a mixture thereof, including at least one dicarboxylic acid and/or a salt thereof;
    about 0.2 to about 15 wt. % of at least one amine including one or more alkanolamines selected from monoethanolamine, diethanolamine, triethanolamine, monoisopropanolamine, diisopropanolamine, N-dimethylamino-ethanolamine, 2-amino-2-methyl-1-propanol, triisopropanolamine, 2-amino-2-methyl-1,3-propanediol, 3-amino-1,2-propanediol, 3-dimethylamino-1,2-propanediol, tris(hydroxymethylamino)methane, and a mixture thereof;
    about 0.05 to about 8 wt. % of at least one cationic polymer selected from poly(methacryloyloxyethyl trimethylammonium chloride), polyquaternium-37, quaternized cellulose derivatives, polyquaternium-4, polyquaternium-6, polyquaternium-10, polyquaternium-11, cationic alkyl polyglycosides, cationized honey, cationic guar derivatives, polymeric dimethyl diallyl ammonium salts and copolymers thereof with esters and amides of acrylic acid and methacrylic acid, copolymers of vinyl pyrrolidone with quaternized derivatives of dialkylaminoalkyl acrylate and methacrylate, vinyl pyrrolidone-vinyl imidazolium methochloride copolymers, quaternized polyvinyl alcohol, polyquaternium-2, polyquaternium-7, polyquaternium-17, polyquaternium-18, polyquaternium-24, polyquaternium-27, polyquaternium-72, and a mixture thereof;
    about 0.5 to about 15 wt. % of at least one alkoxysilane selected from 3-mercaptopropyltriethoxysilane and/or 3-aminopropyltriethoxysilane;
    about 0.5 to about 15 wt. % of at least one polyol selected from hexylene glycol, butylene glycol, and a mixture thereof; and
    at least 50 wt. % of water;
and
(b) a second phase comprising:
    Polysilicone-29;
    at least one silicone oil selected from cyclopentasiloxane, polydimethylsiloxane, and a mixture thereof;
    optionally, at least one non-silicone oil; and
    optionally, at least one organic solvent selected from polyols, C2 to C8 monoalcohols, and a mixture thereof;
wherein the weight ratio of the first phase (a) to the second phase (b) ranges from about 2:0.5 to about 5:1.

25. A method of treating hair, the method comprising applying the composition of claim 1 to hair.

26. A method of treating hair, the method comprising applying the composition of claim 24 to hair.

27. A hair treatment system comprising:
(a) a first phase comprising:
    at least one non-polymeric mono, di, or tricarboxylic acid, and/or a salt thereof, and a mixture thereof;
    at least one amine selected from diamines, polyamines, alkylamines, alkanolamines, and a mixture thereof;
    at least one cationic polymer;
    at least one alkoxysilane selected from 3-mercaptopropyltriethoxysilane and/or 3-aminopropyltriethoxysilane;
    at least one polyol; and
    water;
and
(b) a second phase comprising:
    Polysilicone-29; and
    at least one silicone oil;
wherein the first phase and the second phase are combined as one component, or
wherein the first phase and the second phase are separate components;
wherein the weight ratio of the first phase (a) to the second phase (b) ranges from about 2:0.5 to about 5:1.

* * * * *